United States Patent
Yukawa et al.

(10) Patent No.: US 10,669,376 B2
(45) Date of Patent: Jun. 2, 2020

(54) CURED FILM-FORMING COMPOSITION

(71) Applicant: NISSAN CHEMICAL CORPORATION, Tokyo (JP)

(72) Inventors: Shojiro Yukawa, Funabashi (JP); Yuki Hoshino, Funabashi (JP); Kayo Takeda, Funabashi (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 25 days.

(21) Appl. No.: 16/088,442

(22) PCT Filed: Mar. 30, 2017

(86) PCT No.: PCT/JP2017/013167
§ 371 (c)(1),
(2) Date: Sep. 25, 2018

(87) PCT Pub. No.: WO2017/170828
PCT Pub. Date: Oct. 5, 2017

(65) Prior Publication Data
US 2019/0085130 A1  Mar. 21, 2019

(30) Foreign Application Priority Data

| Mar. 31, 2016 | (JP) | 2016-070121 |
| Sep. 21, 2016 | (JP) | 2016-184455 |
| Feb. 14, 2017 | (JP) | 2017-025372 |

(51) Int. Cl.

| C08G 73/10 | (2006.01) |
| C08G 18/83 | (2006.01) |
| C09D 5/25 | (2006.01) |
| C08L 33/26 | (2006.01) |
| C08F 12/20 | (2006.01) |
| C09D 201/04 | (2006.01) |
| C08L 101/00 | (2006.01) |
| C09D 133/16 | (2006.01) |
| C07C 231/12 | (2006.01) |
| C08L 33/24 | (2006.01) |
| C08F 220/54 | (2006.01) |
| C08F 2/50 | (2006.01) |

(Continued)

(52) U.S. Cl.
CPC ........ *C08G 73/1039* (2013.01); *C07C 231/12* (2013.01); *C08F 2/50* (2013.01); *C08F 220/54* (2013.01); *C08L 33/24* (2013.01); *C08L 33/26* (2013.01); *C08L 101/00* (2013.01); *C09D 7/40* (2018.01); *C09D 133/16* (2013.01); *C09D 133/24* (2013.01); *C09D 133/26* (2013.01); *C09D 201/04* (2013.01); *C08K 5/1575* (2013.01); *C08K 5/45* (2013.01); *C08L 2203/202* (2013.01)

(58) Field of Classification Search
None
See application file for complete search history.

(56) References Cited

U.S. PATENT DOCUMENTS

| 4,125,672 A | 11/1978 | Kakuchi et al. |
| 2003/0109626 A1 | 6/2003 | Bradley et al. |

(Continued)

FOREIGN PATENT DOCUMENTS

| JP | S52-090269 A | 7/1977 |
| JP | S61-148208 A | 7/1986 |
| JP | 2004-531617 A | 10/2004 |
| JP | 2010-275498 A | 12/2010 |
| WO | WO 2006/137366 A1 | 12/2006 |

OTHER PUBLICATIONS

A partial machine translation of JP61-148208, 7 pages, Jul. 5, 1986, Japan.*

(Continued)

*Primary Examiner* — Tae H Yoon
(74) *Attorney, Agent, or Firm* — Leydig, Voit & Mayer, Ltd.

(57) ABSTRACT

Provided are: a cured film-forming composition whereby a underlayer film for image formation formed from the composition exhibits high liquid repellency (lyophobicity) and lyophilic/liquid-repellent properties of the underlayer film can be easily changed even when exposed to a low amount of ultraviolet radiation; and a cured film obtained using the composition. The cured film-forming resin composition is characterized by containing: a polymer comprising a structural unit derived from a first monomer having the structure of formula (1) as component (A); a polymer other than component (A), which is a polymer in which the content of fluorine relative to the overall weight of the polymer is lower than in component (A), as component (B); a photoacid generator as component (C); and a solvent. (In the formula, $R^1$ denotes hydrogen or a methyl group, and $R^2$ denotes a fluorine-containing group able to be detached together with the oxygen atom bonded to $R^2$.)

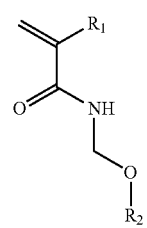

(1)

18 Claims, No Drawings

(51) Int. Cl.
*C09D 133/24* (2006.01)
*C09D 7/40* (2018.01)
*C09D 133/26* (2006.01)
*C08K 5/45* (2006.01)
*C08K 5/1575* (2006.01)

(56) References Cited

U.S. PATENT DOCUMENTS

2010/0159201 A1 6/2010 Maeda et al.
2012/0077126 A1 3/2012 Mori et al.

OTHER PUBLICATIONS

Japanese Patent Office, International Search Report in International Patent Application No. PCT/JP2017/013167 (dated Jul. 4, 2017).

* cited by examiner

CURED FILM-FORMING COMPOSITION

CROSS-REFERENCE TO RELATED APPLICATIONS

This patent application is the U.S. national phase of International Patent Application No. PCT/JP2017/013167, filed Mar. 30, 2017, which claims the benefit of Japanese Patent Application No. 2016-070121, filed on Mar. 31, 2016, Japanese Patent Application No. 2016-184455, filed on Sep. 21, 2016, and Japanese Patent Application No. 2017-025372, filed on Feb. 14, 2017, which are incorporated by reference in their entireties herein.

TECHNICAL FIELD

The present invention relates to a cured film forming composition containing a polymer having a fluoroalkyl group, and further relates to a cured film and an electronic device each formed using the composition.

BACKGROUND ART

In the production process for electronic devices, upon patterning of electrodes and functional thin films, application of the technique for applying a material to intended separate regions utilizing a difference of the wettability with a liquid to the patterning of functional thin films has been proposed. This technique is a method in which a patterning layer having a region that is wettable with a liquid and another region that is unwettable with the liquid is formed on the surface of a substrate, then a liquid containing a material for forming a functional thin film is applied onto the patterning layer, and subsequently dried to form a functional thin film only on the region that is wettable with the liquid, to produce, for example, a wiring in an electronic device.

In order to prevent the liquid from spreading to a region other than the intended portion in carrying out printing using the image forming liquid used in the above-mentioned patterning of electrodes by various printing methods, such as ink-jet or screen printing, it is necessary to exclusively make the intended portion hydrophilic while keeping the surface of the region other than the intended portion hydrophobic.

In recent years, extensive studies have been made on the technique for applying a coating functional material to intended separate regions, by utilizing the finding that the contact angle of a polyimide film can be changed along with the change in the hydrophilic/hydrophobic property of the polyimide by appropriately selecting a polyimide precursor containing a hydrophobic side chain or a polyimide obtained from such a polyimide precursor as a patterning layer for electrodes, functional thin films or the like.

For example, the properties of a wettability changing layer obtained using a polyimide precursor or polyimide having an aliphatic ring are disclosed (see, for example, Patent Literature 1). The literature presumes that cleavage of the aliphatic ring of polyimide is one of the causes of changing the polyimide to be hydrophilic or hydrophobic. It also presumes that, as the amount of side chain (that is, the number of side chains) is increased, the surface energy (critical surface tension) of the polyimide is reduced, so that the polyimide becomes lyophobic.

Further, the examples of the literature show such results that, when a polyamic acid was obtained using an acid dianhydride having an aliphatic ring and a diamine having a hydrocarbon group in the side chain, and the polyamic acid was used in a wettability changing layer, irradiation of the layer with an ultraviolet light largely changed the hydrophilic/hydrophobic property of the layer. They further show that an electrode layer comprising PEDOT/PSS was formed on the wettability changing layer to produce an electronic device.

CITATION LIST

Patent Literature

Patent Literature 1: WO 2006/137366 A1

SUMMARY OF INVENTION

Technical Problem

Generally, an image forming liquid is designed to have a surface tension lower than that of water so that a film can be formed from the liquid. For this reason, many image forming liquids are of a system of organic solvent having a surface tension lower than that of water, taking their easy application into consideration.

However, with respect to the hydrophobic side chain described in the above-mentioned literature, even when the amount of the side chain contained therein is satisfactorily increased, the hydrophobicity (i.e., water repellency) of the unexposed portion of the layer is not satisfactorily high. For example, a problem arises in that when the image forming liquid spreads to the unexposed portion, the image forming liquid is dried at that portion, so that an intended image cannot be obtained. Further, the wettability changing layer has no crosslinked structure formed therein and therefore, a problem occurs in that the wettability changing layer is disadvantageously dissolved depending on the type of the solvent used in the image forming liquid.

The present invention has been made in view of the above. An object of the present invention is to provide a resin composition for forming a cured film, which is advantageous in that an underlayer film for forming an image, which is formed from the resin composition, has a high liquid repellency (lyophobicity); that the lyophilicity or liquid repellency can be easily changed by using a small dose of an ultraviolet light for exposure; and that the lyophilic portion of the film has a high solvent resistance.

Solution to Problem

The present inventors have conducted extensive and intensive studies with a view toward achieving the above-mentioned object. As a result, it has been found that, use of a polymer comprising a structural unit derived from a specific monomer having a fluorine-containing side chain capable of being eliminated provides a film that permits a large change of its lyophilicity or liquid repellency by irradiation with an ultraviolet light. The present invention has been completed based on the finding.

The present invention encompasses the followings.

[1] A resin composition for forming a cured film, comprising:

as component (A), a polymer comprising a structural unit derived from a first monomer having a structure of formula (1) below;

as component (B), a polymer other than component (A), which has a smaller fluorine content based on the weight of the polymer than that of component (A);

a photo-acid generator as component (C); and
a solvent:

[Formula 1]

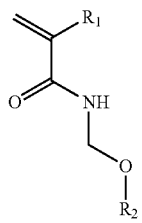

(1)

wherein $R^1$ represents hydrogen or a methyl group, and $R^2$ represents a fluorine-containing group capable of being eliminated together with an oxygen atom to which the fluorine-containing group is bonded.

[2] The resin composition for forming a cured film according to item [1] above, wherein $R^2$ represents a fluorine-substituted hydrocarbon group, which is optionally branched and/or cyclized, and which is optionally interrupted by an aromatic ring, —O—, —S—, —CO—, —CS—, —NH—, or a combination thereof.

[3] The resin composition for forming a cured film according to item [1] or [2] above, wherein $R^2$ has two or more carbon atoms.

[4] The resin composition for forming a cured film according to any one of items [1] to [3] above, wherein the polymer component (A) further comprises a structural unit derived from a second monomer having a group (group (x)) capable of forming due to heat a covalent bond between the polymers as component (A) or between the polymer component (A) and the polymer component (B).

[5] The resin composition for forming a cured film according to any one of items [1] to [4] above, wherein the polymer component (B) comprises a structural unit derived from a monomer having a group (group (x)) capable of forming due to heat a covalent bond between the polymers as component (B) or between the polymer component (A) and the polymer component (B).

[6] The resin composition for forming a cured film according to item [4] or [5] above, wherein group (x) is at least one group selected from the group consisting of a hydroxyl group, a carboxyl group, an amide group, an alkoxysilyl group, an isocyanate group, a blocked isocyanate group, and a group represented by the following formula (2):

[Formula 2]

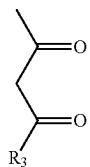

(2)

wherein $R^3$ represents an alkyl group, an alkoxy group, or a phenyl group.

[7] The resin composition for forming a cured film according to any one of items [4] to [6] above, which further comprises, as a component (D), a compound having two or more groups capable of undergoing a thermal reaction with group (x) per molecule.

[8] The resin composition for forming a cured film according to any one of items [1] to [7] above, wherein the polymer component (A) has a fluorine content of 5% by weight or more based on the weight of the polymer.

[9] The resin composition for forming a cured film according to any one of items [1] to [8] above, wherein the polymer component (B) has a fluorine content of less than 5% by weight based on the weight of the polymer.

[10] A cured film, which is obtained using the resin composition for forming a cured film according to any one of items [1] to [9] above, and wherein the cured film has an ultraviolet light exposed portion more lyophilic than an unexposed portion.

[11] The cured film according to item [10] above, wherein the ultraviolet light exposed portion has a contact angle to propylene glycol monomethyl ether acetate at least 5° greater than that of the unexposed portion.

[12] A wiring forming auxiliary layer comprising the cured film of item [10] or [11] above.

[13] Use of a polymer comprising a structural unit derived from a first monomer having a structure of formula (1) below for the manufacture of a resin composition for forming a cured film:

[Formula 3]

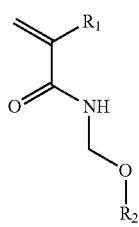

(1)

wherein $R^1$ represents hydrogen or a methyl group, and $R^2$ represents a fluorine-containing group capable of being eliminated together with an oxygen atom to which the fluorine-containing group is bonded.

[14] Use of a copolymer comprising a structural unit derived from a first monomer having a structure of formula (1) below, and a structural unit derived from a second monomer having a group (group (x)) capable of forming due to heat a covalent bond between the polymers as component (A) or between the polymer component (A) and the polymer component (B) for the manufacture of a resin composition for forming a cured film:

[Formula 4]

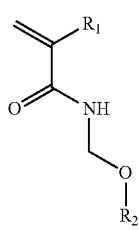

(1)

wherein $R^1$ represents hydrogen or a methyl group, and $R^2$ represents a fluorine-containing group capable of being eliminated together with an oxygen atom to which the fluorine-containing group is bonded.

[15] Use of the resin composition for forming a cured film according to any one of items [1] to [9] above for the manufacture of a cured film having an ultraviolet light exposed portion more lyophilic than an unexposed portion.

[16] The use according to item [15] above, wherein the ultraviolet light exposed portion has a contact angle to propylene glycol monomethyl ether acetate at least 5° greater than that of the unexposed portion.

Advantageous Effects of Invention

The resin composition for forming a cured film of the present invention comprising a polymer comprising a structural unit derived from a specific monomer having a fluorine-containing side chain capable of being eliminated is advantageous in that a large change in the contact angle, that is, a change from lyophilicity to liquid repellency and vice versa, as compared to an image forming liquid using a solvent having a low surface tension as a main solvent, can be imparted to a film formed from the resin composition by irradiating the film with an ultraviolet light. Therefore, utilizing such properties, an underlayer film capable of forming an image for functional materials, such as an electrode, can be formed.

Moreover, the cured film formed from the composition of the present invention is advantageous in that an image forming liquid can be applied to the cured film not only by an ink-jet method but also by various methods, such as spin coating and dipping methods. Therefore the composition is a material effective in productivity.

DESCRIPTION OF EMBODIMENTS

In the present invention, there is provided a resin composition which is advantageously used for forming, on the surface of a substrate, a cured film that is an underlayer film for forming an image having a lyophilic region and a liquid repellent region.

The resin composition of the present invention is applied onto a substrate to form an undried coating film. In this instance, the fluorine-rich polymer (component (A)) and fluorine-poor polymer (component (B)) contained in the resin composition of the present invention form two layers or a concentration gradient so that the fluorine-poor polymer is present in a relatively high concentration on the side of the film in contact with the substrate.

Then, the undried coating film is dried by heating to form a cured film for patterning. In this instance, crosslinking occurs in the fluorine-rich polymer, in the fluorine-poor polymer, or between the fluorine-rich polymer and the fluorine-poor polymer, so that the cured film for patterning becomes insoluble in an image forming liquid. Further, the cured film for patterning is fixed in a state such that the fluorine-poor polymer is present in a relatively high concentration on the side of the film in contact with the substrate and the fluorine-rich polymer is present in a relatively high concentration on the outer surface side of the film.

The cured film for patterning is irradiated with an ultraviolet light in a pattern form. In this instance, the irradiation dose may be lower than the irradiation dose used in a prior art technique. Then, the coating film is subjected to heat treatment. The heat treatment of the coating film in the presence of an acid generated from the photo-acid generator contained in the resin composition of the present invention allows the UV-exposed region of the fluorine-rich polymer present at the surface in a relatively high concentration to release a fluorine-containing group (for example, in the form of an alcohol molecule), to cause self-crosslinking. Therefore, the region exposed to an ultraviolet light loses liquid repellency and is changed to be lyophilic. Thus, from the cured film for patterning, an underlayer film for forming an image having a lyophilic region and a liquid repellent region can be efficiently created. The region which has been changed to be lyophilic can selectively accept the image forming liquid.

The cured film forming composition of the present invention is a resin composition for forming a cured film, comprising: as component (A), a polymer comprising a structural unit derived from a monomer having a structure of formula (1) below; as component (B), a polymer having a smaller fluorine content based on the weight of the polymer than that of component (A); a photo-acid generator as component (C); and a solvent:

[Formula 5]

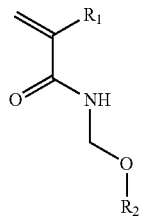

(1)

wherein $R^1$ represents hydrogen or a methyl group, and $R^2$ represents a fluorine-containing group capable of being eliminated together with an oxygen atom to which the fluorine-containing group is bonded.

Further, the cured film forming composition may contain a crosslinking agent as component (D) in addition to components (A), (B), and (C) and the solvent. Further, the cured film forming composition may contain another additive in such an amount that the effects of the present invention are not sacrificed.

Hereinbelow, the present invention will be described according to the items shown below.

1. Component (A)
2. Component (B)
3. Component (C)
4. Component (D)
5. Other additives
6. Solvent
7. Preparation of Cured Film Forming Composition
8. Method for Producing Coating Film and Cured Film
9. Use as Underlayer Film for Forming Image: Method for Producing Electrode for Forming Image 1. Component (A)

Component (A) contained in the cured film forming composition of the present invention is a polymer comprising a structural unit derived from a first monomer having a structure of formula (1) above. Component (A) is a fluorine-rich polymer which has a high fluorine content as compared to component (B). And, when the resin composition of the present invention is applied onto a substrate, the fluorine-rich polymer component (A) is present in a relatively high concentration on the outer surface side of the applied layer. It is preferred that the polymer component (A) has a fluorine content of 5% by weight or more based on the weight of the polymer.

Component (A) contained in the cured film forming composition of the present invention is a polymer comprising a structural unit derived from a monomer having at least a structure of formula (1) above (wherein $R^1$ and $R^2$ are as defined above).

The polymer component (A) in the present invention includes a polymer obtained by conducting copolymerization using a monomer having an unsaturated double bond, such as an acrylate, a methacrylate, styrene, or a derivative thereof, in addition to the monomer having a structure of formula (1) above.

Accordingly, component (A) in the present invention includes:

(a) a homopolymer comprising one species of the monomer having a structure of formula (1) above;

(b) a copolymer comprising two or more species of the monomers having a structure of formula (1) above; and (c) a copolymer comprising (one species of or two or more species of) the monomer or monomers having a structure of formula (1) above and a monomer having an unsaturated double bond, such as an acrylate, a methacrylate, styrene, or a derivative thereof.

The polymer component (A) (hereinafter, referred to also as "specific copolymer") may be a polymer having the above-mentioned structure. There is no particular limitation to the scaffold of the backbone chain constituting the polymer and the type of the side chain.

The polymer component (A) preferably has a weight average molecular weight of 1,000 to 200,000, more preferably 2,000 to 150,000, further preferably 3,000 to 100,000. When the weight average molecular weight of the polymer is more than 200,000 and too large, the resultant resin composition is likely to be reduced in the solubility in a solvent, causing the handling properties to be poor. When the weight average molecular weight of the polymer is less than 1,000 and too small, the resultant resin composition is likely to be unsatisfactorily cured upon heat curing, causing the solvent resistance and heat resistance to be poor. The weight average molecular weight is a value obtained by gel permeation chromatography (GPC) using polystyrene as a standard sample. Hereinafter, this applies to the present description.

In formula (1), $R^2$ represents a fluorine-containing group capable of being eliminated together with an oxygen atom to which the fluorine-containing group is bonded.

$R^2$ preferably represents a fluorine-substituted hydrocarbon group.

The hydrocarbon group may be branched and/or cyclized. Further, the hydrocarbon group may be interrupted by an aromatic ring, —O—, —S—, —CO—, —CS—, —NH—, or a combination thereof. Examples of such interrupting groups include phenylene, naphthylene, biphenylene, ether, thioether, carbonyl, carboxyl, amide, and urea, but the interrupting group is not limited to these groups.

The number of carbon atoms in $R^2$ is preferably two or more, more preferably 2 to 18, and most preferably 2 to 10.

When $R^2$ in formula (1) is a fluorine-substituted hydrocarbon group, a representative example of $R^2$ is a fluoroalkyl group.

The number of carbon atoms in the fluoroalkyl group is preferably two or more, 2 to 50, 2 to 30, 2 to 18, 2 to 10, 4 to 10, and 4 to 8 in increasing preference. The fluorine-substituted hydrocarbon group may be branched and/or cyclized.

Examples of such fluoroalkyl groups include a 2,2,2-trifluoroethyl group, a 2,2,3,3,3-pentafluoropropyl group, a 2-(perfluorobutyl)ethyl group, a 3-perfluorobutyl-2-hydroxypropyl group, a 2-(perfluorohexyl)ethyl group, a 3-perfluorohexyl-2-hydroxypropyl group, a 2-(perfluorooctyl) ethyl group, a 3-perfluorooctyl-2-hydroxypropyl group, a 2-(perfluorodecyl)ethyl group, a 2-(perfluoro-3-methylbutyl)ethyl group, a 3-(perfluoro-3-methylbutyl)-2-hydroxypropyl group, a 2-(perfluoro-5-methylhexyl)ethyl group, a 2-(perfluoro-5-methylhexyl)-2-hydroxypropyl group, a 2-(perfluoro-7-methyloctyl)ethyl group, and a 2-(perfluoro-7-methyloctyl)-2-hydroxypropyl group.

When $R^2$ in formula (1) is a fluorine-substituted hydrocarbon group optionally interrupted by —O—, a representative example of $R^2$ is a fluoroalkyl ether group.

For example, it includes Rf group (a) comprising a polyfluoroether structure represented by the following Formula 1.

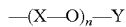     Formula 1

In Formula 1, X represents a divalent saturated hydrocarbon group having 1 to 10 carbon atoms or a fluorinated, divalent saturated hydrocarbon group having 1 to 10 carbon atoms, wherein the substituents in each of the units bracketed with subscript n may be the same or different; Y represents a hydrogen atom (only when a fluorine atom is not bonded to the carbon atom adjacent to the oxygen atom adjacent to Y), a monovalent saturated hydrocarbon group having 1 to 20 carbon atoms, or a fluorinated, monovalent saturated hydrocarbon group having 1 to 20 carbon atoms, and n represents an integer of 2 to 50. The total number of the fluorine atoms in Formula 1 is 2 or more.

With respect to X and Y in Formula 1, preferably, X represents an alkylene group having 1 to 10 carbon atoms, which is fluorinated except for one hydrogen atom, or a perfluorinated alkylene group having 1 to 10 carbon atoms, wherein the substituents in each of the units bracketed with subscript n may be the same or different; and Y represents an alkyl group having 1 to 20 carbon atoms, which is fluorinated except for one hydrogen atom, or a perfluorinated alkyl group having 1 to 20 carbon atoms.

With respect to X and Y in Formula 1, more preferably, X represents a perfluorinated alkylene group having 1 to 10 carbon atoms, wherein the substituents in each of the units bracketed with subscript n may be the same or different; and Y represents a perfluorinated alkyl group having 1 to 20 carbon atoms.

In Formula 1, n represents an integer of 2 to 50. Preferably, n is 2 to 30, more preferably, n is 2 to 15. When n is 2 or more, a better liquid repellency can be provided. When n is 50 or less, elimination of the liquid repellent group is likely to occur at the exposed portion, so that a better lyophilicity can be obtained.

Further, the total number of the carbon atoms in Rf group (a) comprising a polyfluoroether structure represented by Formula 1 is preferably two or more, 2 to 50, 2 to 30, 2 to 18, 2 to 10, 4 to 10, and 4 to 8 in increasing preference. When the total number of the carbon atoms falls within the above-mentioned range, the polymer component (A) exhibits a better liquid repellency.

Specific examples of X include —$CF_2$—, —$CF_2CF_2$—, —$CF_2CF_2CF_2$—, —$CF_2CF(CF_3)$—, —$CF_2CF_2CF_2CF_2$—, —$CF_2CF_2CF(CF_3)$—, and $CF_2CF(CF_3)CF_2$—.

Specific examples of Y include —$CF_3$, —$CF_2CF_3$, —$CF_2CHF_2$, —$(CF_2)_2CF_3$, —$(CF_2)_3CF_3$, —$(CF_2)_4CF_3$, —$(CF_2)_5CF_3$, —$(CF_2)_6CF_3$, —$(CF_2)_7CF_3$, —$(CF_2)_8CF_3$, —$(CF_2)_9CF_3$, $(CF_2)_{11}CF_3$, and —$(CF_2)_{15}CF_3$.

A preferred Rf group (a) comprising a polyfluoroether structure represented by Formula 1 is a Rf group (a) represented by Formula 2.

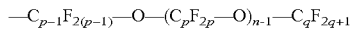     Formula 2

In Formula 2, p represents an integer of 2 or 3, wherein the integers in each of the units bracketed with subscript n are the same; q represents an integer of 1 to 20; and n represents an integer of 2 to 50.

Specifically, in view of ease of synthesis, preferred examples of Rf group (a) represented by Formula 2 include:

—CF$_2$O(CF$_2$CF$_2$O)$_{n-1}$CF$_3$ (wherein n is 2 to 9),

—CF(CF$_3$)O(CF$_2$CF(CF$_3$)O)$_{n-1}$C$_6$F$_{13}$ (wherein n is 2 to 6), and

—CF(CF$_3$)O(CF$_2$CF(CF$_3$)O)$_{n-1}$C$_3$F$_7$ (wherein n is 2 to 6).

Rf groups (a) in the polymer component (A) may be the same or different.

As mentioned above, an acid generated from the photo-acid generator (described below in detail) contained in the resin composition of the present invention allows the portion of the polymer component (A) exposed to an ultraviolet light to release a fluorine-containing group (for example, in the form of an alcohol molecule) from the structure of formula (1), so as to cause crosslinking.

In addition to the structure of formula (1), the polymer component (A) may further comprise a structural unit derived from a second monomer having a group (group (x)) capable of forming due to heat a covalent bond between the polymers as component (A) or between the polymer component (A) and the polymer component (B). (The crosslinking agent optionally added separately is described below in the item for component (D).)

Group (x) is preferably at least one group selected from the group consisting of a hydroxyl group, a carboxyl group, an amide group, an alkoxysilyl group, an isocyanate group, a blocked isocyanate group, and a group represented by the following formula (2):

[Formula 6]

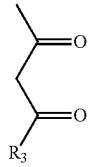
(2)

wherein R$^3$ represents an alkyl group, an alkoxy group, or a phenyl group.

Of these, a hydroxyl group, a carboxyl group, or an amide group is preferred.

The above thermally reacting site may form a covalent bond with another polymer component (A) or the polymer component (B) through a direct bond or a linking group. Such a linking group includes a divalent group selected from a linear alkylene group having 1 to 15 carbon atoms, a branched alkylene group having 3 to 20 carbon atoms, a cyclic alkylene group having 3 to 20 carbon atoms, and a phenylene group, or a group formed from a plurality of the divalent groups bonded to each other. In this case, examples of the bonds between the divalent groups constituting the linking group and those of the bonds between the linking group and the thermally reacting site include a single bond, an ester linkage, an amide linkage, an urea linkage, and an ether linkage. When a plurality of the divalent groups are used, the divalent groups may be the same or different. When a plurality of the bonds are used, the bonds may be the same or different.

Examples of the linear alkylene groups having 1 to 15 carbon atoms include a methylene group, an ethylene group, a n-propylene group, a n-butylene group, a n-pentylene group, a n-hexylene group, a n-heptylene group, a n-octylene group, a n-nonylene group, a n-decylene group, a n-undecylene group, a n-dodecylene group, a n-tridecylene group, a n-tetradecylene group, and a n-pentadecylene group.

Examples of the branched alkylene groups having 3 to 20 carbon atoms include an i-propylene group, an i-butylene group, a s-butylene group, a t-butylene group, a 1-methyl-n-butylene group, a 2-methyl-n-butylene group, a 3-methyl-n-butylene group, a 1,1-dimethyl-n-propylene group, a 1,2-dimethyl-n-propylene group, a 2,2-dimethyl-n-propylene group, a 1-ethyl-n-propylene group, a 1-methyl-n-pentylene group, a 2-methyl-n-pentylene group, 3-methyl-n-pentylene group, a 4-methyl-n-pentylene group, a 1,1-dimethyl-n-butylene group, a 1,2-dimethyl-n-butylene group, a 1,3-dimethyl-n-butylene group, a 2,2-dimethyl-n-butylene group, a 2,3-dimethyl-n-butylene group, a 3,3-dimethyl-n-butylene group, a 1-ethyl-n-butylene group, a 2-ethyl-n-butylene group, a 1,1,2-trimethyl-n-propylene group, a 1,2,2-trimethyl-n-propylene group, a 1-ethyl-1-methyl-n-propylene group, a 1-ethyl-2-methyl-n-propylene group, and alkylene groups having up to 20 carbon atoms and being branched at any position.

Examples of the cyclic alkylene groups having 3 to 20 carbon atoms include monocyclic alkylene groups, such as a cyclopropylene group, a cyclobutylene group, a cyclopentylene group, a cyclohexylene group, a cycloheptylene group, and a cyclooctylene group; and polycyclic alkylene groups, such as a norbornylene group, a tricyclodecylene group, a tetracyclododecylene group, and an adamantylene group.

In formula (2) above, examples of alkyl groups indicated by R$^3$ include alkyl groups having 1 to 20 carbon atoms, and preferred are alkyl groups having 1 to 5 carbon atoms.

Examples of such alkyl groups include a methyl group, an ethyl group, a n-propyl group, an i-propyl group, a n-butyl group, an i-butyl group, a s-butyl group, a t-butyl group, a n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a n-heptyl group, a n-octyl group, a n-nonyl group, a n-decanyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosyl group, a cyclopropyl group, a cyclobutyl group, a cyclopentyl group, a cyclohexyl group, and a cycloheptyl group.

Of these, for example, a methyl group, an ethyl group, a n-propyl group, a n-butyl group, and an isobutyl group are preferred.

In formula (2) above, examples of alkoxy groups indicated by R$^3$ include alkoxy groups having 1 to 20 carbon atoms. Preferred are alkoxy groups having 1 to 5 carbon atoms.

Examples of such alkoxy groups include a methoxy group, an ethoxy group, a n-propoxy group, an i-propoxy group, a n-butoxy group, an i-butoxy group, a s-butoxy group, a t-butoxy group, a n-pentoxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, a n-hexyloxy group, a 1-methyl-n-pentyloxy group, a 2-methyl-n-pentyloxy group, a 3-methyl-n-pentyloxy group, a 4-methyl-n-pentyloxy group, a 1,1-dimethyl-n-butoxy group, a 1,2-dimethyl-n-butoxy group, a 1,3-dimethyl-n-butoxy group, a 2,2-dimethyl-n-butoxy group, a 2,3-dimethyl-n-butoxy group, a 3,3-dimethyl-n-butoxy group, a 1-ethyl-n-butoxy group, a 2-ethyl-n-butoxy group, a 1,1,2-trimethyl-n-propoxy group, a 1,2,2,-trimethyl-n-propoxy group, a 1-ethyl-1-methyl-n-propoxy group, a 1-ethyl-2-methyl-n-propoxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group, a n-eicosadecyloxy group, a cyclopropoxy group, a cyclobutoxy group, a cyclopentyloxy group, a cyclohexyloxy group, and a cycloheptyloxy group.

Of these, for example, a methoxy group, an ethoxy group, and a n-propoxy group are preferred.

An easy way of carrying out the method for synthesizing a copolymer comprising the a structural unit derived from a first monomer represented by formula (1), and a structural unit derived from a second monomer having a group (group (x)) capable of forming due to heat a covalent bond between the polymers as component (A) or between the polymer component (A) and the polymer component (B), preferably having at least one group (x) selected from the group consisting of a hydroxyl group, a carboxyl group, an amide group, an alkoxysilyl group, an isocyanate group, a blocked isocyanate group, and a group represented by formula (2) above would be polymerization of the first monomer having a structure of formula (1) with the second monomer having a group (group (x)) capable of forming due to heat a covalent bond between the polymers as component (A) or between the polymer component (A) and the polymer component (B), preferably having at least one group (x) selected from the group consisting of a hydroxyl group, a carboxyl group, an amide group, an alkoxysilyl group, an isocyanate group, a blocked isocyanate group, and a group represented by formula (2) above.

Examples of the monomers having at least one group (x) selected from the group consisting of a hydroxyl group, a carboxyl group, an amide group, an alkoxysilyl group, an isocyanate group, a blocked isocyanate group, and a group represented by formula (2) above include monomers having a hydroxyl group, such as 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, 2,3-dihydroxypropyl acrylate, 2,3-dihydroxypropyl methacrylate, glycerol monomethacrylate, diethylene glycol monoacrylate, diethylene glycol monomethacrylate, caprolactone 2-(acryloyloxy)ethyl ester, caprolactone 2-(methacryloyloxy)ethyl ester, poly(ethylene glycol) acrylate, poly(propylene glycol) acrylate, poly(ethylene glycol) ethyl ether acrylate, poly(ethylene glycol) ethyl ether methacrylate, 5-acryloyloxy-6-hydroxynorbornene-2-carboxylic-6-lactone, and 5-methacryloyloxy-6-hydroxynorbornene-2-carboxylic-6-lactone; monomers having a carboxyl group, such as acrylic acid, methacrylic acid, crotonic acid, mono-(2-(acryloyloxy)ethyl) phthalate, mono-(2-(methacryloyloxy)ethyl) phthalate, N-(carboxyphenyl)maleimide, N-(carboxyphenyOmethacrylamide, and N-(carboxyphenyl)acrylamide; monomers having a phenolic hydroxyl group, such as hydroxystyrene, N-(hydroxyphenyl)methacrylamide, N-(hydroxyphenyl)acrylamide, N-(hydroxyphenyl)maleimide, and N-(hydroxyphenyl)maleimide; monomers having an amide group, such as acrylamide, methacrylamide, N-methylacrylamide, N,N-dimethylacrylamide, and N,N-diethylacrylamide; monomers having an alkoxysilyl group, such as 3-acryloyloxytrimethoxysilane, 3-acryloyloxytriethoxysilane, 3-methacryloyloxytrimethoxysilane, and 3-methacryloyloxytriethoxysilane; monomers having a group represented by formula (2) above, such as 2-acetoacetoxyethyl acrylate and 2-acetoacetoxyethyl methacrylate (ethylene glycol monoacetoacetate monomethacrylate); monomers having an isocyanate group, such as 2-acryloyloxyethyl isocyanate and 2-methacryloyloxyethyl isocyanate; and monomers having a blocked isocyanate group, such as 2-(0-[1'-methylpropylideneamino]carboxyamino)ethyl methacrylate, 2-[(3,5-dimethylpyrazolyl)carbonylamino]ethyl methacrylate, and diethyl 2-((2-(methacryloyloxy)ethyl)carbamoyl)malonate.

Further, component (A) contained in the resin composition for forming a cured film of the present invention may be a copolymer having a structural unit derived from a monomer represented by formula (1), a structural unit derived from a monomer having at least one group (x) selected from the group consisting of a hydroxyl group, a carboxyl group, an amide group, an alkoxysilyl group, an isocyanate group, a blocked isocyanate group, and a group represented by formula (2) above, and a structural unit derived from a monomer other than the above-mentioned monomers.

An easy way of carrying out the method for synthesizing the above-mentioned copolymer would be polymerization of the monomer represented by formula (1), the monomer having at least one group (x) selected from the group consisting of a hydroxyl group, a carboxyl group, an amide group, an alkoxysilyl group, an isocyanate group, a blocked isocyanate group, and a group represented by formula (2) above (hereinafter, a hydroxyl group, a carboxyl group, an amide group, an alkoxysilyl group, an isocyanate group, a blocked isocyanate group, and a group represented by formula (2) above are referred to also as "specific functional group 1"), with a monomer other than the above-mentioned monomers (hereinafter, referred to also as "third monomer").

The monomer represented by formula (1) and the monomer having at least one group (x) are as described above. The third monomer means a monomer other than the first and second monomers.

Specific examples of such monomers include acrylate compounds, methacrylate compounds, maleimide compounds, acrylonitrile, maleic anhydride, styrene compounds, and vinyl compounds.

Specific examples of the third monomers are shown below, but the third monomer is not limited to these compounds.

Examples of the acrylate compounds include methyl acrylate, ethyl acrylate, isopropyl acrylate, benzyl acrylate, naphthyl acrylate, anthryl acrylate, anthrylmethyl acrylate, phenyl acrylate, 2,2,2-trifluoroethyl acrylate, tert-butyl acrylate, cyclohexyl acrylate, isobornyl acrylate, 2-methoxyethyl acrylate, methoxytriethylene glycol acrylate, 2-ethoxyethyl acrylate, tetrahydrofurfuryl acrylate, 3-methoxybutyl acrylate, 2-methyl-2-adamantyl acrylate, 2-propyl-2-adamantyl acrylate, 8-methyl-8-tricyclodecyl acrylate, and 8-ethyl-8-tricyclodecyl acrylate.

Examples of the methacrylate compounds include methyl methacrylate, ethyl methacrylate, isopropyl methacrylate, benzyl methacrylate, naphthyl methacrylate, anthryl methacrylate, anthrylmethyl methacrylate, phenyl methacrylate, 2,2,2-trifluoroethyl methacrylate, tert-butyl methacrylate, cyclohexyl methacrylate, isobornyl methacrylate, 2-methoxyethyl methacrylate, methoxytriethylene glycol methacrylate, 2-ethoxyethyl methacrylate, tetrahydrofurfuryl methacrylate, 3-methoxybutyl methacrylate, 2-methyl-2-adamantyl methacrylate, γ-butyrolactone methacrylate, 2-propyl-2-adamantyl methacrylate, 8-methyl-8-tricyclodecyl methacrylate, and 8-ethyl-8-tricyclodecyl methacrylate.

Examples of the vinyl compounds include methylvinyl ether, benzylvinyl ether, vinylnaphthalene, vinylcarbazole, allylglycidyl ether, and 3-ethenyl-7-oxabicyclo[4.1.0]heptane.

Examples of the styrene compounds include styrene, methylstyrene, chlorostyrene, and bromostyrene.

Examples of the maleimide compounds include maleimide, N-methylmaleimide, N-phenylmaleimide, and N-cyclohexylmaleimide.

In order to obtain the specific copolymer, the amount of the monomer represented by formula (1) ranges preferably 10 to 90 mol %, and the amount of the monomer having at least one group (x) selected from the group consisting of a hydroxyl group, a carboxyl group, an amide group, an alkoxysilyl group, an isocyanate group, a blocked isocyanate group, and a group represented by formula (2) above ranges preferably 10 to 90 mol %, both based on the total mole of the monomers. When the amount of the contained monomer having specific functional group 1 is less than 10 mol %, it may be difficult to impart satisfactory heat curing properties, so that the solvent resistance of the resultant cured film would be difficult to maintain.

When the third monomer is used in obtaining the specific copolymer, the amount of the third monomer used is preferably 90 mol % or less based on the total mole of the monomers.

There is no particular limitation to the method for obtaining the specific copolymer used in the present invention. For example, the specific copolymer can be obtained by subjecting a solution of the first and second monomers and, if desired, the third monomer, a polymerization initiator and others, in a solvent to polymerization reaction at a temperature of 50 to 110° C. There is no particular limitation to the solvent used in this reaction as long as the solvent can dissolve therein the first and second monomers, and the third monomer, a polymerization initiator and others used as occasion demands. Specific examples of the solvents are described in <Solvent> below.

The specific copolymer obtained by the above-mentioned method is generally in a solution state in which the specific copolymer is dissolved in a solvent.

The solution of the specific copolymer obtained by the above-mentioned method may be subjected to reprecipitation by pouring the solution into, e.g., diethyl ether or water while stirring, and the formed precipitate may be subjected to filtration and washed, and then dried at room temperature or dried by heating under atmospheric pressure or under a reduced pressure, to obtain a powder of the specific copolymer. By the above-mentioned operation, it is possible to remove the polymerization initiator and unreacted monomers coexisting with the specific copolymer, so that a powder of the purified specific copolymer can be obtained. When satisfactory purification cannot be made by a single operation, the obtained powder may be redissolved in a solvent to repeat the above-mentioned operation.

In the present invention, the specific copolymer may be used in the form of a powder or in the form of a solution obtained by redissolving the purified powder in the below-mentioned solvent.

Further, in the present invention, the specific copolymer component (A) may be in the form of a mixture of a plurality of the specific copolymers.

2. Component (B)

Component (B) contained in the cured film forming composition of the present invention is a polymer other than component (A), wherein the polymer has a smaller fluorine content based on the weight of the polymer than that of component (A). Component (B) is a fluorine-poor polymer which contains no fluorine atom or a very slight amount of a fluorine atom, and, when the resin composition of the present invention is applied onto a substrate, the fluorine-poor polymer component (B) is present at a relatively high concentration on the substrate side of the applied layer. It is preferred that the polymer component (B) has a fluorine content of less than 5% by weight based on the weight of the polymer.

Component (B) contained in the resin composition for forming a cured film of the present invention may be a polymer containing a structural unit derived from a monomer having a structure of formula (1) above; however, it has a smaller content of the structural unit based on the weight of the polymer than that of component (A).

The resin composition for forming a cured film of the present invention is in the form of the so-called polymer blend obtained by mixing together component (A) and another polymer component (B).

By appropriately controlling, for example, the structures of the polymers (components (A) and (B) and other polymers) contained in the polymer blend, it may be possible to create a concentration gradient of each of the polymers within the cured film formed from the polymer blend along the thickness of the film. Thus, polymer blending may be utilized as an effective means.

For example, change of the lyophilicity or liquid repellency of the film depends only to the nature of the surface of the film. From this point of view, the polymer having a fluoroalkyl group in the present invention may need to be present only in the upper layer (surface layer) of the cured film.

The proportion of each of the components incorporated is described below in the item for "Preparation of the cured film forming composition".

Use of the polymer blending permits reduction of the amount of the fluorine-containing compound used, which is usually expensive. As the result, an inexpensive material having satisfactory performance may be obtained. Further, selection of component (B) having an appropriate structure permits providing such additional advantages as improved film forming properties and enhanced adhesion to the substrate.

As mentioned above, in order to form a cured film having a low liquid-repellent layer as the lower layer and a lyophilicity/liquid repellency changing layer as the upper layer, the film may be formed by successively stacking the lower and upper layers; however, such an manner is cumbersome.

Meanwhile, a mixture of a low liquid-repellent material and a material for the lyophilicity/liquid repellency changing layer (that is, the polymer component (A) in the present invention), wherein the material for the upper layer is small in polarity or molecular weight, as compared to the material for the lower layer, is prepared. The mixture is applied to a substrate and dried. While the solvent is evaporated, the material for the upper layer would transfer to the outer surface to form a quasi-layer. It may facilitate the control of the concentration gradient mentioned above (separation into layers in this case).

As a film forming material which can form the lower layer, an acrylic polymer is most preferred.

Examples of the other materials usable as a material for the lower layer include general organic polymers, such as an epoxy resin, an acrylic resin, polypropylene, polyvinyl alcohol, polyvinylphenol, polyisobutylene, polyester, and polyimide.

In the case a polymer blend is used in the application in which the film is required to have a thickness of about 400 nm, the polymer blend preferably contains the polymer component (A) in an amount of at least 5% by weight or more, in order to prevent the resultant cured film from having a large in-plane unevenness of the surface physical properties.

Component (B) is preferably a polymer having a N-alkoxymethyl group and a polymerizable group containing a C=C double bond as a unit structure.

Examples of N of the N-alkoxymethyl group, i.e., nitrogen atom of the N-alkoxymethyl group, include a nitrogen atom of amide, a nitrogen atom of thioamide, a nitrogen atom of urea, a nitrogen atom of thiourea, a nitrogen atom of urethane, and a nitrogen atom bonded to the site adjacent to a nitrogen atom of a nitrogen-containing heterocycle. Therefore, an example of the structure of the N-alkoxymethyl group includes a structure in which an alkoxymethyl group is bonded to a nitrogen atom selected from, for example, a nitrogen atom of amide, a nitrogen atom of thioamide, a nitrogen atom of urea, a nitrogen atom of thiourea, a nitrogen atom of urethane, and a nitrogen atom bonded to the site adjacent to a nitrogen atom of a nitrogen-containing heterocycle.

The monomer which gives a N-alkoxymethyl group may be a monomer having the above-mentioned group, but preferred examples include compounds represented by the following formula (b1).

[Formula 7]

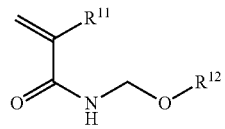

(b1)

Wherein $R^{11}$ represents a hydrogen atom or a methyl group, and $R^{12}$ represents a hydrogen atom or a linear or branched alkyl group having 1 to 10 carbon atoms.

Examples of the alkyl groups include a methyl group, an ethyl group, a n-propyl group, an isopropyl group, a n-butyl group, an isobutyl group, a sec-butyl group, a tert-butyl group, a n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a n-heptyl group, a 1-methyl-n-hexyl group, a 2-methyl-n-hexyl group, a 3-methyl-n-hexyl group, a 1,1-dimethyl-n-pentyl group, a 1,2-dimethyl-n-pentyl group, a 1,3-dimethyl-n-pentyl group, a 2,2-dimethyl-n-pentyl group, a 2,3-dimethyl-n-pentyl group, a 3,3-dimethyl-n-pentyl group, a 1-ethyl-n-pentyl group, a 2-ethyl-n-pentyl group, a 3-ethyl-n-pentyl group, a 1-methyl-1-ethyl-n-butyl group, a 1-methyl-2-ethyl-n-butyl group, a 1-ethyl-2-methyl-n-butyl group, a 2-methyl-2-ethyl-n-butyl group, a 2-ethyl-3-methyl-n-butyl group, a n-octyl group, a 1-methyl-n-heptyl group, a 2-methyl-n-heptyl group, a 3-methyl-n-heptyl group, a 1,1-dimethyl-n-hexyl group, a 1,2-dimethyl-n-hexyl group, a 1,3-dimethyl-n-hexyl group, a 2,2-dimethyl-n-hexyl group, a 2,3-dimethyl-n-hexyl group, a 3,3-dimethyl-n-hexyl group, a 1-ethyl-n-hexyl group, a 2-ethyl-n-hexyl group, a 3-ethyl-n-hexyl group, a 1-methyl-1-ethyl-n-pentyl group, a 1-methyl-2-ethyl-n-pentyl group, a 1-methyl-3-ethyl-n-pentyl group, a 2-methyl-2-ethyl-n-pentyl group, a 2-methyl-3-ethyl-n-pentyl group, a 3-methyl-3-ethyl-n-pentyl group, a n-nonyl group, and a n-decyl group.

Specific examples of such monomers include acrylamide compounds or methacrylamide compounds substituted with a hydroxymethyl group or an alkoxymethyl group, such as N-hydroxymethyl(meth)acrylamide, N-methoxymethyl (meth)acrylamide, N-ethoxymethyl(meth)acrylamide, and N-butoxymethyl(meth)acrylamide. The term "(meth)acrylamide" means both methacrylamide and acrylamide.

The polymer component (B) may comprise a structural unit derived from a monomer having a group (group (x)) capable of forming due to heat a covalent bond with another polymer component (B) or with the polymer component (A).

For example, the cured film forming composition of the present invention may contain, as component (B), a compound having at least two groups (x) selected from the group consisting of a hydroxyl group, a carboxyl group, an amide group, an alkoxysilyl group, an isocyanate group, a blocked isocyanate group, and a group represented by formula (2) above (hereinafter, referred to also as "specific functional group 2").

Examples of polymer compounds as component (B) include an acrylic polymer, polyamic acid, polyimide, polyvinyl alcohol, polyester, polyester polycarboxylic acid, polyether polyol, polyester polyol, polycarbonate polyol, polycaprolactone polyol, polyalkyleneimine, polyallylamine, celluloses (cellulose and derivatives thereof), polymers having a linear structure or a branched structure, such as a phenolic novolak resin, and cyclic polymers, such as cyclodextrins.

Preferred examples of polymer compounds as component (B) include an acrylic polymer, cyclodextrins, celluloses, polyether polyol, polyester polyol, polycarbonate polyol, polycaprolactone polyol, and a phenolic novolak resin.

The acrylic polymer, which is a preferred example of the polymer compound as component (B), may be a polymer which is obtained by polymerizing a monomer having an unsaturated double bond, such as acrylic acid, methacrylic acid, styrene, or a vinyl compound, and is obtained by polymerizing a monomer having group (x) or a mixture thereof. There is no particular limitation to the scaffold of the polymer backbone chain constituting the acrylic polymer, the type of the side chain, and the like.

Examples of monomers having at least one group (x) selected from the group consisting of a hydroxyl group, a carboxyl group, an amide group, an alkoxysilyl group, an isocyanate group, a blocked isocyanate group, and a group represented by formula (2) above include monomers having a hydroxyl group, such as 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, 2,3-dihydroxypropyl acrylate, 2,3-dihydroxypropyl methacrylate, diethylene glycol monoacrylate, diethylene glycol monomethacrylate, caprolactone 2-(acryloyloxy)ethyl ester, caprolactone 2-(methacryloyloxy)ethyl ester, poly(ethylene glycol) ethyl ether acrylate, poly(ethylene glycol) ethyl ether methacrylate, 5-acryloyloxy-6-hydroxynorbornene-2-carboxylic-6-lactone, and 5-methacryloyloxy-6-hydroxynorbornene-2-carboxylic-6-lactone; monomers having a carboxyl group, such as acrylic acid, methacrylic acid, crotonic acid, mono-(2-(acryloyloxy)ethyl) phthalate, mono-(2-(methacryloyloxy)ethyl) phthalate, N-(carboxyphenyl)maleimide, N-(carboxyphenyl)methacrylamide, and N-(carboxyphenyl)acrylamide; monomers having a phenolic hydroxyl group, such as hydroxystyrene, N-(hydroxyphenyl)methacrylamide, N-(hydroxyphenyl)acrylamide, N-(hydroxyphenyl)maleimide, and N-(hydroxyphenyl)maleimide; monomers having an amide group, such as acrylamide, methacrylamide, N-methylacrylamide, N,N-dimethylacrylamide, and N,N-diethylacrylamide; monomers having an alkoxysilyl group, such as 3-acryloyloxytrimethoxysilane, 3-acryloyloxytriethoxysilane, 3-methacryloyloxytrimethoxysilane, and 3-methacryloyloxytriethoxysilane; monomers having a group represented by formula (2) above, such as 2-acetoacetoxyethyl acrylate and 2-acetoacetoxyethyl methacrylate (ethylene glycol monoacetoacetate monomethacrylate); monomers having an isocyanate group, such as 2-acryloyloxyethyl isocyanate and 2-methacryloyloxyethyl isocyanate; and monomers having a blocked isocyanate group, such as 2-(0-[1'-methylpropylideneamino]carboxyamino)ethyl methacrylate, 2-[(3,5-dimethylpyrazolyl)carbonylamino]ethyl methacrylate, and diethyl 2-((2-(methacryloyloxy)ethyl)carbamoyl)malonate.

Further, in the present invention, when synthesizing an acrylic polymer which is an example of component (B), a monomer having no specific functional group 2 may be used in such an amount that the effects of the present invention are not sacrificed.

Specific examples of such monomers include acrylate compounds, methacrylate compounds, maleimide compounds, acrylonitrile, maleic anhydride, styrene compounds, and vinyl compounds.

Examples of acrylate compounds include methyl acrylate, ethyl acrylate, isopropyl acrylate, benzyl acrylate, naphthyl acrylate, anthryl acrylate, anthrylmethyl acrylate, phenyl acrylate, 2,2,2-trifluoroethyl acrylate, tert-butyl acrylate, cyclohexyl acrylate, isobornyl acrylate, 2-methoxyethyl acrylate, methoxytriethylene glycol acrylate, 2-ethoxyethyl acrylate, tetrahydrofurfuryl acrylate, 3-methoxybutyl acrylate, 2-methyl-2-adamantyl acrylate, 2-propyl-2-adamantyl acrylate, 8-methyl-8-tricyclodecyl acrylate, and 8-ethyl-8-tricyclodecyl acrylate.

Examples of methacrylate compounds include methyl methacrylate, ethyl methacrylate, isopropyl methacrylate, benzyl methacrylate, naphthyl methacrylate, anthryl methacrylate, anthrylmethyl methacrylate, phenyl methacrylate, 2,2,2-trifluoroethyl methacrylate, tert-butyl methacrylate, cyclohexyl methacrylate, isobornyl methacrylate, 2-methoxyethyl methacrylate, methoxytriethylene glycol methacrylate, 2-ethoxyethyl methacrylate, tetrahydrofurfuryl methacrylate, 3-methoxybutyl methacrylate, 2-methyl-2-adamantyl methacrylate, 2-propyl-2-adamantyl methacrylate, 8-methyl-8-tricyclodecyl methacrylate, and 8-ethyl-8-tricyclodecyl methacrylate.

Examples of maleimide compounds include maleimide, N-methylmaleimide, N-phenylmaleimide, and N-cyclohexylmaleimide.

Examples of styrene compounds include styrene, methylstyrene, chlorostyrene, and bromostyrene.

Examples of vinyl compounds include vinyl ether, methylvinyl ether, benzylvinyl ether, phenylvinyl ether, and propylvinyl ether.

The amount of the monomer having specific functional group 2 used for obtaining the acrylic polymer, which is an example of component (B), ranges preferably 2 to 100% by weight based on the total weight of the monomers used for obtaining the acrylic polymer component (B). When the amount of the monomer having specific functional group 2 is too small, the application properties of the obtained cured film are likely to be unsatisfactory.

When a monomer having no specific functional group 2 is used in obtaining the acrylic polymer, the amount of the monomer used is preferably 98% by weight or less based on the total weight of the monomers.

With respect to the method for obtaining the acrylic polymer which is an example of component (B), there is no particular limitation. For example, the acrylic polymer is obtained by subjecting a solution of the monomer having specific functional group 2 and, if desired, a monomer having no specific functional group 2, a polymerization initiator and others in a solvent to polymerization reaction at a temperature of 50 to 110° C. There is no particular limitation to the solvent used in this reaction as long as the solvent can dissolve therein the monomer having specific functional group 2 and the monomer having no specific functional group 2, and polymerization initiator and others used as occasion demands. Specific examples of solvents are described in the item for <Solvent> below.

The acrylic polymer as an example of component (B) obtained by the above-mentioned method is usually in a solution state in which the acrylic polymer is dissolved in a solvent.

The solution of the acrylic polymer as an example of component (B) obtained by the above-mentioned method is subjected to reprecipitation by pouring the solution into, e.g., diethyl ether or water while stirring, and the formed precipitate is subjected to filtration and washed, and then dried at room temperature or dried by heating under atmospheric pressure or under a reduced pressure, to obtain a powder of the acrylic polymer as an example of component (B). By the above-mentioned operation, it is possible to remove the polymerization initiator and unreacted monomers coexisting with the acrylic polymer as an example of component (B), so that a powder of the purified acrylic polymer as an example of component (B) may be obtained. When satisfactory purification cannot be made by a single operation, the obtained powder may be redissolved in a solvent to repeat the above-mentioned operation.

The acrylic polymer, which is a preferred example of component (B), preferably has a weight average molecular weight of 3,000 to 200,000, more preferably 4,000 to 150,000, further preferably 5,000 to 100,000. When the weight average molecular weight of the acrylic polymer is more than 200,000 and too large, the resultant resin composition is likely to be reduced in the solubility in a solvent, causing the handling properties to be poor. When the weight average molecular weight of the acrylic polymer is less than 3,000 and too small, the resultant resin composition is likely to be unsatisfactorily cured upon heat curing, causing the solvent resistance and heat resistance to be poor.

Examples of cyclodextrins, which are a preferred example of the polymer compound as component (B), include cyclodextrins, such as α-cyclodextrin, β-cyclodextrin, and γ-cyclodextrin; methylated cyclodextrins, such as methyl-α-cyclodextrin, methyl-β-cyclodextrin, and methyl-γ-cyclodextrin; and hydroxyalkylcyclodextrins, such as hydroxymethyl-α-cyclodextrin, hydroxymethyl-β-cyclodextrin, hydroxymethyl-γ-cyclodextrin, 2-hydroxyethyl-α-cyclodextrin, 2-hydroxyethyl-β-cyclodextrin, 2-hydroxyethyl-γ-cyclodextrin, 2-hydroxypropyl-α-cyclodextrin, 2-hydroxypropyl-β-cyclodextrin, 2-hydroxypropyl-γ-cyclodextrin, 3-hydroxypropyl-α-cyclodextrin, 3-hydroxypropyl-β-cyclodextrin, 3-hydroxypropyl-γ-cyclodextrin, 2,3-dihydroxypropyl-α-cyclodextrin, 2,3-dihydroxypropyl-β-cyclodextrin, and 2,3-dihydroxypropyl-γ-cyclodextrin, and, for example, hydroxyalkylcyclodextrins are preferred.

Examples of celluloses, which are a preferred example of the polymer compound as component (B), include hydroxyalkyl celluloses, such as hydroxyethyl cellulose and hydroxypropyl cellulose; hydroxyalkylalkyl celluloses, such as hydroxyethylmethyl cellulose, hydroxypropylmethyl cellulose, and hydroxyethylethyl cellulose; and celluloses, and, for example, preferred are hydroxyalkyl celluloses, such as hydroxyethyl cellulose and hydroxypropyl cellulose.

Examples of polyether polyols, which are a preferred example of the polymer compound as component (B), include those which are obtained by adding, e.g., propylene oxide, polyethylene glycol, or polypropylene glycol to a polyhydric alcohol, such as polyethylene glycol, polypropylene glycol, propylene glycol, bisphenol A, triethylene glycol, or sorbitol. Specific examples of polyether polyols include ADEKA POLYETHER P Series, G Series, EDP Series, BPX Series, FC Series, CM Series, manufactured by ADEKA Corporation; and UNIOX (registered trademark) HC-40, HC-60, ST-30E, ST-40E, G-450, G-750, UNIOL (registered trademark) TG-330, TG-1000, TG-3000, TG-4000, HS-1600D, DA-400, DA-700, DB-400, NONION (registered trademark) LT-221, ST-221, OT-221, manufactured by NOF Corporation.

Examples of polyester polyols, which are a preferred example of the polymer compound as component (B), include those which are obtained by reacting a diol, such as ethylene glycol, propylene glycol, butylene glycol, polyethylene glycol, or polypropylene glycol, with a polycarboxylic acid, such as adipic acid, sebacic acid, or isophthalic acid. Specific examples of polyester polyols include POLYLITE (registered trademark) OD-X-286, OD-X-102, OD-X-355, OD-X-2330, OD-X-240, OD-X-668, OD-X-2108, OD-X-2376, OD-X-2044, OD-X-688, OD-X-2068, OD-X-2547, OD-X-2420, OD-X-2523, OD-X-2555, OD-X-2560, manufactured by DIC Corporation; and Polyol P-510, P-1010, P-2010, P-3010, P-4010, P-5010, P-6010, F-510, F-1010, F-2010, F-3010, P-1011, P-2011, P-2013, P-2030, N-2010, PNNA-2016, manufactured by Kuraray Co., Ltd.

Examples of polycarbonate polyols, which are a preferred example of the polymer compound as component (B), include those which are obtained by reacting, e.g., diethyl carbonate, diphenyl carbonate, or ethylene carbonate with a polyhydric alcohol, such as trimethylolpropane or ethylene glycol. Specific examples of polycarbonate polyols include PLACCEL (registered trademark) CD205, CD205PL, CD210, CD220, manufactured by Daicel Corporation; and Polycarbonate Diol C-590, C-1050, C-2050, C-2090, C-3090, manufactured by Kuraray Co., Ltd.

Examples of polycaprolactone polyols, which are a preferred example of the polymer compound as component (B), include those which are obtained by subjecting s-caprolactone to ring-opening polymerization using a polyhydric alcohol, such as trimethylolpropane or ethylene glycol, as an initiator. Specific examples of polycaprolactone polyols include POLYLITE (registered trademark) OD-X-2155, OD-X-640, OD-X-2568, manufactured by DIC Corporation; and PLACCEL (registered trademark) 205, L205AL, 205U, 208, 210, 212, L212AL, 220, 230, 240, 303, 305, 308, 312, 320, manufactured by Daicel Corporation.

Examples of phenolic novolak resins, which are a preferred example of the polymer compound as component (B), include a phenol-formaldehyde polycondensation product.

In the resin composition for forming a cured film of the present invention, the compound as component (B) may be used in the form of a powder or in the form of a solution obtained by redissolving the purified powder in the below-mentioned solvent.

Further, in the resin composition for forming a cured film of the present invention, component (B) may be a single species of compound, or in the form of a mixture of a plurality of the compounds shown as examples of component (B).

The amount of component (B) contained in the resin composition for forming a cured film of the present invention ranges, relative to 10 parts by mass of component (A), preferably 5 to 95 parts by mass, more preferably 30 to 95 parts by mass, 50 to 95 parts by mass, 60 to 95 parts by mass, and 80 to 95 parts by mass in increasing preference. When the amount of component (B) contained is too large, there is a problem in that the image forming ability becomes poor. When the amount of component (B) contained is too small, there is a problem in that the film forming properties become poor.

3. Component (C)

The resin composition for forming a cured film according to the present embodiment may further contain a photo-acid generator as component (C) in addition to components (A) and (B) and the solvent.

There is no particular limitation to the photo-acid generator as component (C) as long as it generates an acid by photodecomposition upon irradiation with an ultraviolet light.

Examples of acids generated from the photo-acid generator by photodecomposition include hydrochloric acid, sulfonic acids, such as methanesulfonic acid, ethanesulfonic acid, propanesulfonic acid, butanesulfonic acid, pentanesulfonic acid, octanesulfonic acid, benzenesulfonic acid, p-toluenesulfonic acid, camphor sulfonic acid, trifluoromethanesulfonic acid, p-phenolsulfonic acid, 2-naphthalenesulfonic acid, mesitylenesulfonic acid, p-xylene-2-sulfonic acid, m-xylene-2-sulfonic acid, 4-ethylbenzenesulfonic acid, 1H,1H,2H,2H-perfluorooctanesulfonic acid, perfluoro(2-ethoxyethane)sulfonic acid, pentafluoroethanesulfonic acid, nonafluorobutane-1-sulfonic acid, and dodecylbenzenesulfonic acid, and hydrates and salts thereof.

Examples of compounds which generate an acid due to a light include bis(tosyloxy)ethane, bis(tosyloxy)propane, bis(tosyloxy)butane, p-nitrobenzyl tosylate, o-nitrobenzyl tosylate, 1,2,3-phenylenetris(methyl sulfonate), pyridinium p-toluenesulfonate, morpholinium p-toluenesulfonate, ethyl p-toluenesulfonate, propyl p-toluenesulfonate, butyl p-toluenesulfonate, isobutyl p-toluenesulfonate, methyl p-toluenesulfonate, phenethyl p-toluenesulfonate, cyanomethyl p-toluenesulfonate, 2,2,2-trifluoroethyl p-toluenesulfonate, 2-hydroxybutyl p-toluenesulfonate, N-ethyl-p-toluenesulfonamide, and compounds represented by the following formulae [PAG-1] to [PAG-41].
[Formula 8]
[PAG-1]
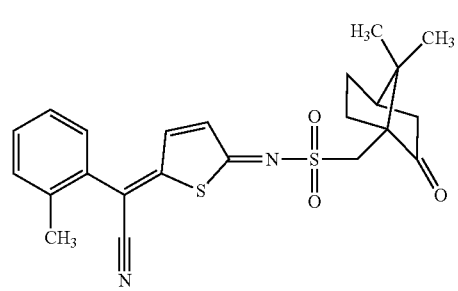
[PAG-2]
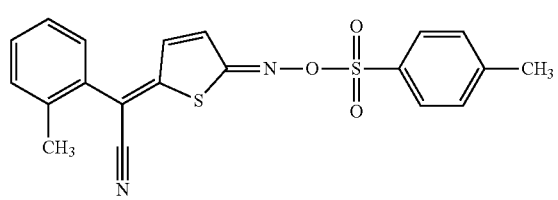
[PAG-3]
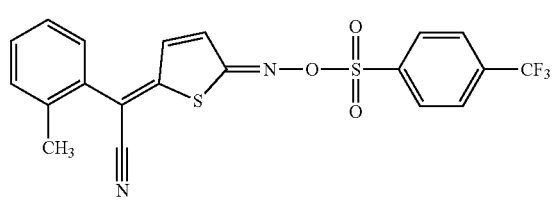
[PAG-4]
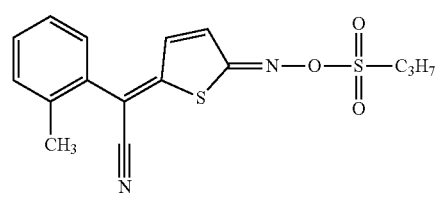
[PAG-5]
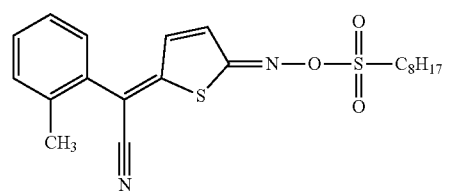
[Formula 9]
[PAG-6]
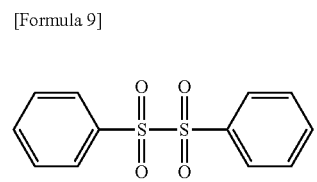
[PAG-7]
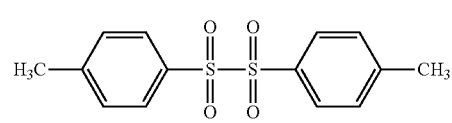
[PAG-8]
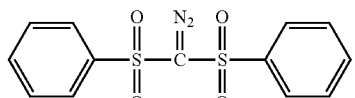
[PAG-9]
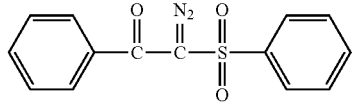
[PAG-10]
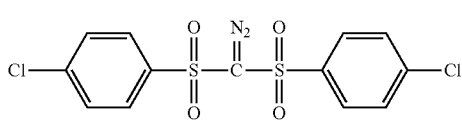
[PAG-11]
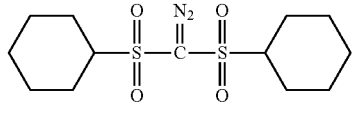
[PAG-12]
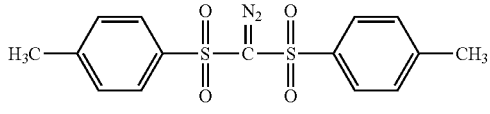
[PAG-13]
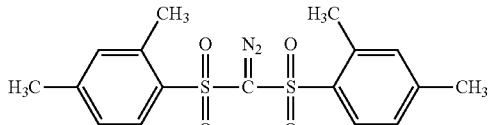
[Formula 10]
[PAG-14]
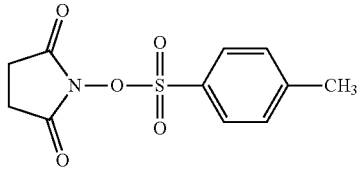
[PAG-15]
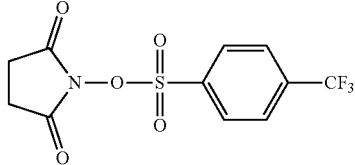
[PAG-16]
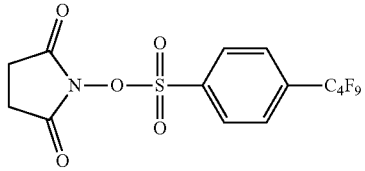
[PAG-17]
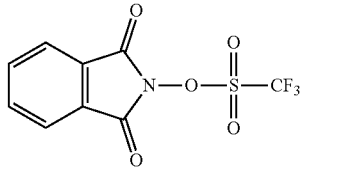

[Formula 11]
[PAG-18] 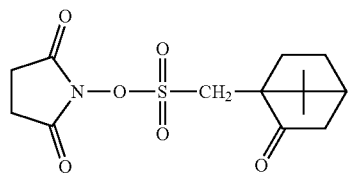
[PAG-19] 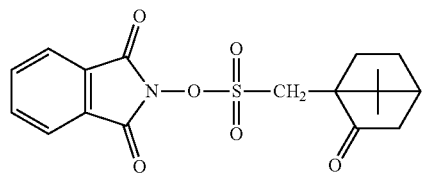
[PAG-20] 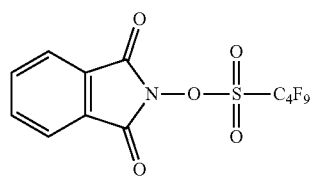
[PAG-21] 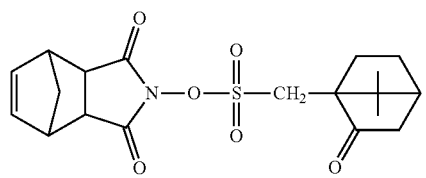
[PAG-22] 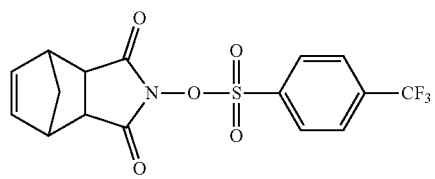
[PAG-23] 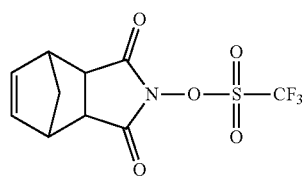
[PAG-24] 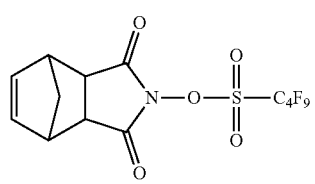
[Formula 12]
[PAG-25] 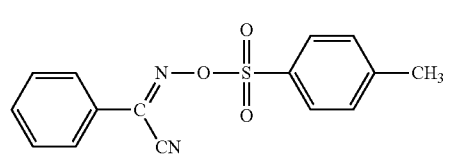
[PAG-26] 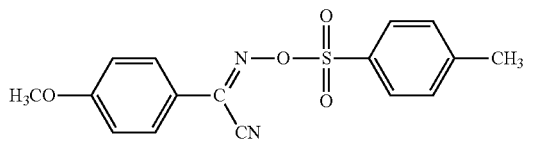
[PAG-27] 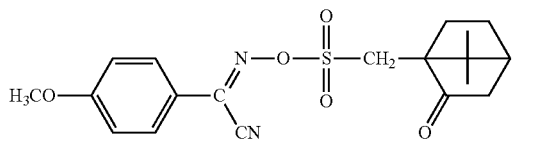
[PAG-28] 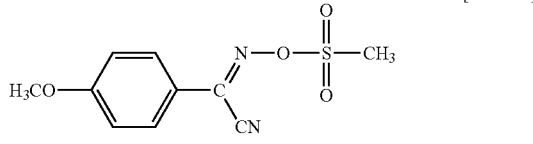
[Formula 13]
[PAG-29] 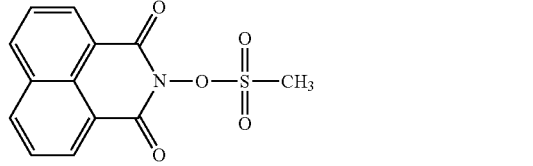
[PAG-30] 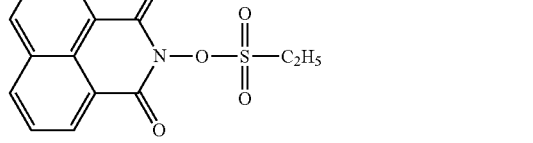
[PAG-31] 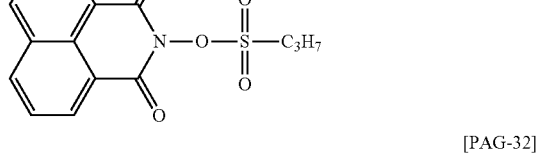
[PAG-32] 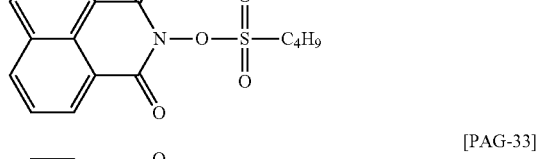
[PAG-33] 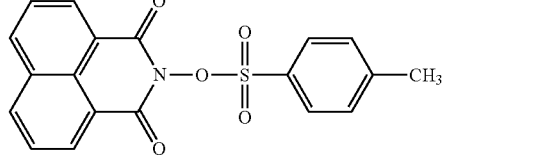
[PAG-34] 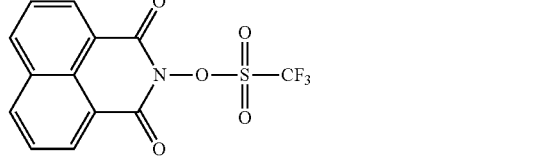

[Formula 14]

[PAG-35]
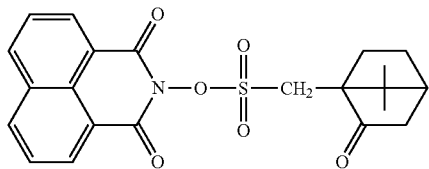

[PAG-36]
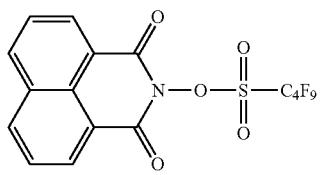

[PAG-37]
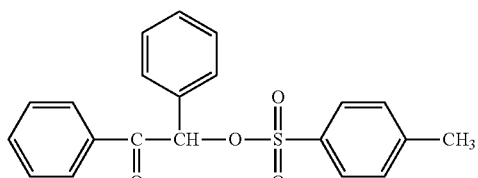

[PAG-38]
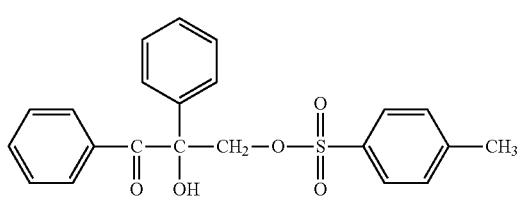

[PAG-39]
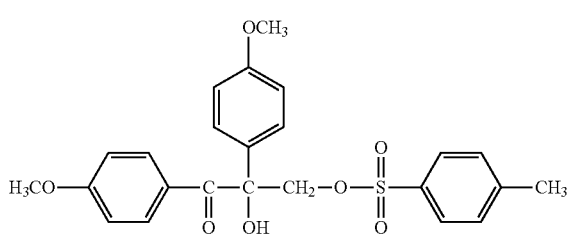

[PAG-40]
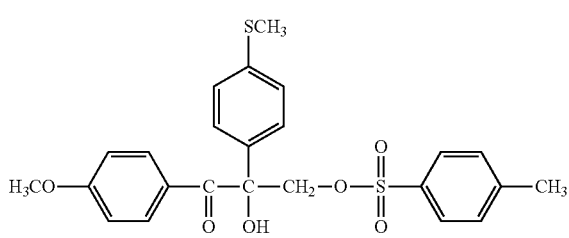

[PAG-41]
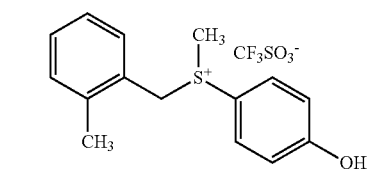

The amount of component (C) contained in the resin composition for forming a cured film of the present invention ranges, relative to 100 parts by mass of the total of the polymer component (A) and the polymer component (B), preferably 0.1 to 20 parts by mass, more preferably 0.5 to 20 parts by mass, further preferably 1 to 15 parts by mass, and most preferably 5 to 15 parts by mass. When the amount of component (C) contained is larger than 20 parts by mass, the storage stability of the composition is likely to become poor.

4. Component (D)

The resin composition for forming a cured film of the present invention may further contain, as component (D), a compound having two or more groups capable of undergoing a thermal reaction with group (x) per molecule. Component (D) is a crosslinking agent optionally introduced into the composition. For example, the crosslinking agent is a compound having a structure which can undergo a thermal reaction with, for example, the hydroxyl group of components (A) and (B), to form a crosslinked structure.

Specific examples of the crosslinking agents are shown below, but the crosslinking agent is not limited to these compounds. With respect to the thermal crosslinking agent, for example, (D-1) a phenoplast compound, (D-2) an epoxy compound, (D-3) a crosslinkable compound having per molecule two or more isocyanate groups or blocked isocyanate groups, and (D-4) a crosslinkable compound having per molecule two or more Meldrum's acid structures are preferred. Further, when group (x) is an isocyanate group, a blocked isocyanate group, or an alkoxysilyl group, a compound having two or more groups (x) per molecule may be used as a crosslinking agent. These crosslinking agents may be used alone or in combination.

Specific examples of phenoplast compounds (D-1) include 2,6-bis(hydroxymethyl)phenol, 2,6-bis(hydroxymethyl)cresol, 2,6-bis(hydroxymethyl)-4-methoxyphenol, 3,3',5,5'-tetrakis(hydroxymethyl)biphenyl-4,4'-diol, 3,3'-methylenebis(2-hydroxy-5-methylbenzenemethanol), 4,4'-(1-methylethylidene)bis[2-methyl-6-hydroxymethylphenol], 4,4'-methylenebis[2-methyl-6-hydroxymethylphenol], 4,4'-(1-methylethylidene)bis[2,6-bis(hydroxymethyl)phenol], 4,4'-methylenebis[2,6-bis(hydroxymethyl)phenol], 2,6-bis(methoxymethyl)phenol, 2,6-bis(methoxymethyl)cresol, 2,6-bis(methoxymethyl)-4-methoxyphenol, 3,3',5,5'-tetrakis(methoxymethyl)biphenyl-4,4'-diol, 3,3'-methylenebis(2-methoxy-5-methylbenzenemethanol), 4,4'-(1-methylethylidene)bis[2-methyl-6-methoxymethylphenol], 4,4'-methylenebis[2-methyl-6-methoxymethylphenol], 4,4'-(1-methylethylidene)bis[2,6-bis(methoxymethyl)phenol], and 4,4'-methylenebis[2,6-bis(methoxymethyl)phenol]. The phenoplast compounds are commercially available, and specific examples of such commercially available phenoplast compounds include 26DMPC, 46DMOC, DM-BIPC-F, DM-BIOC-F, TM-BIP-A, BISA-F, BI25X-DF, BI25X-TPA (each of which is manufactured by Asahi Organic Chemicals Industry Co., Ltd.).

These crosslinkable compounds may be used alone or in combination.

Further, the resin composition for forming a cured film of the present invention may contain an epoxy compound as component (D-2).

As an epoxy compound, for example, a crosslinkable compound represented by formula (d2) may be contained.

[Formula 15]

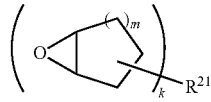

(d2)

wherein k represents an integer of 2 to 10, m represents an integer of 0 to 4, and $R^{21}$ represents a k-valent organic group.

The above-mentioned component is not particularly limited as long as it is a compound having a cycloalkene oxide structure represented by formula (d2). Specific examples of the compounds include formulae D-2-1 and D-2-2 below and commercially available products shown below.

[Formula 16]

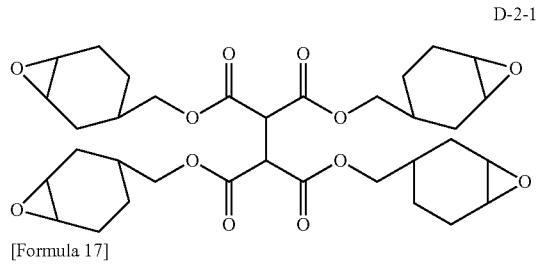

D-2-1

[Formula 17]

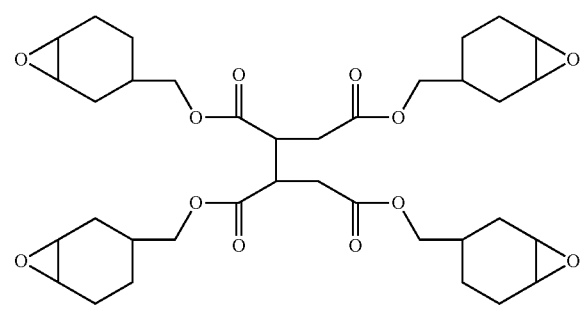

D-2-2

Examples of commercially available products include EPOLEAD GT-401, EPOLEAD GT-403, EPOLEAD GT-301, EPOLEAD GT-302, CELLOXIDE 2021, CELLOXIDE 3000 (trade names; manufactured by Daicel Corporation); Denacol EX-252 which is an alicyclic epoxy resin (trade name; manufactured by Nagase Chemtex Corporation); CY175, CY177, CY179 (trade names; each of which is manufactured by CIBA-GEIGY A.G); ARALDITE CY-182, ARALDITE CY-192, ARALDITE CY-184 (trade names; each of which is manufactured by CIBA-GEIGY A.G); EPICLON 200, EPICLON 400 (trade names; each of which is manufactured by DIC Corporation); EPIKOTE 871, EPIKOTE 872 (trade names; each of which is manufactured by Yuka Shell Epoxy Kabushiki Kaisha); and ED-5661, ED-5662 (trade names; each of which is manufactured by Celanese Corporation). Further, a polymer obtained using, for example, CYCLOMER M-100 (trade name; manufactured by Daicel Corporation) as a raw material may be used.

As the epoxy compound, for example, a compound having a partial structure of Formula (D-2-3) below may be used.

[Formula 18]

Formula (D-2-3)

Wherein p represents an integer of 2 to 10, and $R^{31}$ represents a p-valent organic group.

The epoxy compound is not particularly limited as long as it is a compound having an oxirane structure represented by Formula (D-2-3). Specific examples of such compounds include Formula (D-2-4) and commercially available products shown below.

[Formula 19]

Formula (D-2-4)

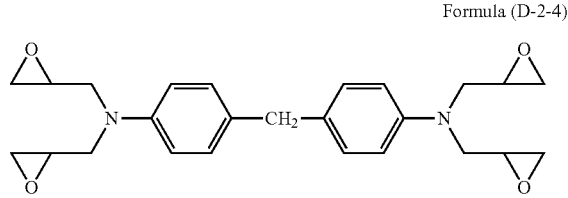

With respect to commercially available products, examples of bisphenol A epoxy resins include "EPIKOTE 828", "EPIKOTE 834", "EPIKOTE 1001", "EPIKOTE 1004" (trade names; each of which is manufactured by Japan Epoxy Resins Co., Ltd.), and "EPICLON 850", "EPICLON 860", "EPICLON 4055" (trade names; each of which is manufactured by DIC Corporation). Examples of bisphenol F epoxy resins include "EPIKOTE 807" (trade name; manufactured by Japan Epoxy Resins Co., Ltd.), and "EPICLON 830" (trade name; manufactured by DIC Corporation). Examples of phenolic novolak epoxy resins include "EPICLON N-740", "EPICLON N-770", "EPICLON N-775" (trade names; each of which is manufactured by DIC Corporation), and "EPIKOTE 152", "EPIKOTE 154" (trade names; each of which is manufactured by Japan Epoxy Resins Co., Ltd.). Examples of cresol novolak epoxy resins include "EPICLON N-660", "EPICLON N-665", "EPICLON N-670", "EPICLON N-673", "EPICLON N-680", "EPICLON N-695", "EPICLON N-665-EXP", "EPICLON N-672-EXP" (trade names; each of which is manufactured by DIC Corporation). Examples of glycidylamine epoxy resins include "EPICLON 430", "EPICLON 430-L" (trade names; manufactured by DIC Corporation), "TETRAD-C", "TETRAD-X" (trade names; each of which is manufactured by Mitsubishi Gas Chemical Company, Inc.), "EPIKOTE 604", "EPIKOTE 630" (trade names; each of which is manufactured by Japan Epoxy Resins Co., Ltd.), "SUMI-EPDXY ELM120", "SUMI-EPDXY ELM100", "SUMI-EPDXY ELM434", "SUMI-EPDXY ELM434HV" (trade names; each of which is manufactured by Sumitomo Chemical Co., Ltd.), "Epotohto YH-434", "Epotohto YH-434L" (trade names; each of which is manufactured by Tohto Kasei Co., Ltd.), and "ARALDITE MY-720" (trade name; manufactured by Asahi-CIBA Limited). Further, a polymer obtained using, for example, glycidyl methacrylate as a raw material can be used.

These crosslinkable compounds can be used alone or in combination.

Component (D-3) is not particularly limited as long as it is a compound having per molecule two or more isocyanate groups or blocked isocyanate groups. Specific examples of such compounds include commercially available products shown below.

Examples of commercially available products include B-830, B-815N, B-842N, B-870N, B-874N, B-882N, B-7005, B-7030, B-7075, B-5010 (each of which is manufactured by Mitsui Chemicals, Inc.), and DURANATE (registered trademark) 17B-60PX, DURANATE TPA-B80E, DURANATE MF-B60X, DURANATE MF-K60X, DURANATE E402-B80T (each of which is manufactured by Asahi Kasei Chemicals Corporation).

Further, a polymer obtained using, e.g., a monomer having a blocked isocyanate group, such as Karenz (registered trademark) AOI, Karenz MOI, Karenz MOI-BM, Karenz MOI-BP, or Karenz MOI-DEM (each of which is manufactured by Showa Denko K.K.), as a raw material may be used.

Component (D-4) is a crosslinkable compound having two or more Meldrum's acid structures per molecule. Especially, preferred are compounds represented by the following formula [A].

[Formula 20]

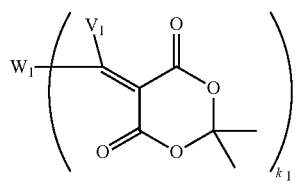

[A]

Wherein $W_1$ represents a $k_1$-valent organic group; $V_1$ represents —H, —OH, —SR, —OR, or —NHR; R represents a monovalent organic group having 1 to 35 carbon atoms and optionally having a benzene ring, a cyclohexane ring, a heterocycle, fluorine, an ether linkage, an ester linkage, or an amide linkage at any position; and $k_1$ represents an integer of 1 to 8.

When $k_1$ is 2, $W_1$ is preferably a $C_2$-$C_{10}$ linear, branched, or cyclic alkylene.

Such a compound and a method for producing the same are described in WO 2012/091089 A1.

The above compound is especially preferably a compound represented by the following formula D4.

[Formula 21]

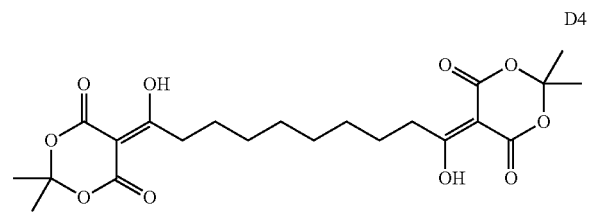

D4

The crosslinking agents represented by formula [A] above may be used alone or in combination.

When group (x) is an isocyanate group, a blocked isocyanate group, or an alkoxysilyl group, a compound having two or more groups (x) per molecule may be used as a crosslinking agent.

Specific examples of the compounds include pentaerythritol, dipentaerythritol, diethylene glycol, triethylene glycol, dipropylene glycol, adipic acid, adipamide, 1-(4-(2-(4-(3-oxo-butyl)-phenoxy)-ethoxy)-phenyl)-butane-1,3-dione, and 1,4-butanediol diacetoacetate.

Of the polymers defined as component (B) as those having two or more groups (x) per molecular chain, a polymer having two or more groups (x) per molecular chain may be used.

Of these, from the viewpoint of the reactivity and solvent resistance, a polymer having a blocked isocyanate group obtained using a crosslinkable compound having a Meldrum's acid structure, or a monomer of diethyl 2-((2-(methacryloyloxy)ethyl)carbamoyl)malonate, as a raw material is preferred.

When a crosslinking agent as component (D) is added, the amount of the crosslinking agent contained ranges 3 to 50 parts by mass, preferably 7 to 40 parts by mass, more preferably 10 to 30 parts by mass, relative to 100 parts by mass of the total of components (A) and (B). When the amount of the crosslinkable compound contained is too small, it is likely that the density of crosslinking formed by the crosslinkable compound is not unsatisfactory, so that the effect of improving the solvent resistance after patterning cannot be obtained. To the contrary, when the amount of the crosslinkable compound contained is more than 50 parts by mass, it is likely that the crosslinkable compound remains uncrosslinked, which would reduce the heat resistance and solvent resistance after patterning as well as the resistance to baking for a long time, and further adversely affect the storage stability of the resin composition for forming the cured film.

5. Other Additives

The resin composition for forming a cured film according to the embodiment of the present invention may contain another additive in such an amount that the effects of the present invention are not sacrificed.

As another additive, for example, a sensitizer may be incorporated. When forming a cured film according to an embodiment of the present invention from the cured film forming composition according to the present embodiment, the sensitizer is effective in promoting the photoreaction.

Examples of sensitizers include derivatives, such as benzophenone, anthracene, anthraquinone, and thioxanthone, and nitrophenyl compounds. Of these, especially preferred are N,N-diethylaminobenzophenone, which is a derivative of benzophenone; and 2-nitrofluorene, 2-nitrofluorenone, 5-nitroacenaphthene, 4-nitrobiphenyl, 4-nitrocinnamic acid, 4-nitrostilbene, 4-nitrobenzophenone, and 5-nitroindole, which are nitrophenyl compounds.

The sensitizer is not particularly limited to those mentioned above. These sensitizers can be used alone or in combination.

In the embodiment of the present invention, the amount of the sensitizer used ranges preferably 0.1 to 20 parts by mass, more preferably 0.2 to 10 parts by mass, relative to 100 parts by mass of the total of components (A), (B), and (C). When the amount of the sensitizer used is too small, it is likely that the effect of the sensitizer cannot be satisfactorily obtained. When the amount of the sensitizer used is too large, it is likely that the transmittance of the cured film formed is reduced or the surface of the film is roughened.

Further, the cured film forming composition according to the embodiment of the present invention may contain the other additives, for example, a silane coupling agent, a surfactant, a rheology modifier, a pigment, a dye, a storage stabilizer, an anti-foaming agent, or an antioxidant in such an amount that the effects of the present invention are not sacrificed.

6. Solvent

The resin composition for forming a cured film of the present invention is usually used in a solution state in which the resin composition is dissolved in a solvent. There is no particular limitation to the type, structure and the like of the solvent used for the solution as long as the solvent has such dissolving power for components (A), (B), and (C) and, if necessary, component (D) and/or other additives.

Specific examples of solvents include ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol, propylene glycol monomethyl ether, propylene glycol monomethyl ether acetate, propylene glycol propyl ether acetate, cyclopentylmethyl ether, isopropyl alcohol, toluene, xylene, methyl ethyl ketone, cyclopentanone, cyclohexanone, 2-butanone, 3-methyl-2-pentanone, 2-pentanone, 2-heptanone, γ-butyrolactone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, N,N-dimethylformamide, N,N-dimethylacetamide, and N-methylpyrrolidone.

These solvents may be used alone or in combination. Of these solvents, propylene glycol monomethyl ether, propylene glycol monomethyl ether acetate, cyclohexanone, 2-heptanone, propylene glycol propyl ether, propylene glycol propyl ether acetate, ethyl lactate, butyl lactate, methyl 3-methoxypropionate, ethyl 3-methoxypropionate, ethyl 3-ethoxypropionate, and methyl 3-ethoxypropionate are more preferred because of their good film forming properties and high safety.

Under the assumption that the substances left behind the removal of the solvent from the resin composition for forming a cured film of the present invention are defined as solids, the content of the solids in the composition ranges, for example, 1 to 30% by mass.

7. Preparation of Cured Film Forming Composition

The resin composition for forming a cured film of the present invention contains; as component (A), a polymer comprising a structural unit derived from a first monomer having a structure of formula (1) above; as component (B), a polymer other than component (A), which has a smaller fluorine content based on the weight of the polymer than that of component (A); a photo-acid generator as component (C); and a solvent. Further, the resin composition may contain a crosslinking agent as component (D). The resin composition may contain another additive in such an amount that the effects of the present invention are not sacrificed.

The incorporation ratio by mass of components (A) to (B) ranges preferably 5:95 to 45:55. Incorporation of component (B) in a too large amount would cause a problem of poor image forming ability. Incorporation of component (B) in a too small amount would cause a problem of poor film forming properties.

Preferred examples of the resin composition for forming a cured film of the present invention are as follows.

[1] A resin composition for forming a cured film, comprising:
as component (A), a polymer comprising a structural unit derived from a first monomer having a structure of formula (1) above, and, as component (B), a polymer other than component (A), which has a smaller fluorine content based on the weight of the polymer than that of component (A), wherein component (A):component (B) mass ratio ranges 5-15:85-95,
0.1 to 20 parts by mass of a photo-acid generator as component (C), relative to 100 parts by mass of the total of the polymer component (A) and the polymer component (B), and
a solvent.

[2] A resin composition for forming a cured film, comprising:
as component (A), a polymer comprising a structural unit derived from a first monomer having a structure of formula (1) above, and, as component (B), a polymer other than component (A), which has a smaller fluorine content based on the weight of the polymer than that of component (A), wherein component (A):component (B) mass ratio is 5-15:85-95,
0.1 to 20 parts by mass of a photo-acid generator as component (C),
3 to 40 parts by mass of component (D), both relative to 100 parts by mass of the total of the polymer component (A) and the polymer component (B), and
a solvent.

The formulation, preparation method and the like of the cured film forming composition of the present invention used in the form of a solution are described below in detail.

There is no particular limitation to the solids content of the cured film forming composition according to the present embodiment as long as the individual components are uniformly dissolved in the solvent. The solids content of the composition may range 1 to 80% by mass, preferably 3 to 60% by mass, more preferably 5 to 40% by mass. The solids refer to the remainder of the removal of the solvent from all of the components in the cured film forming composition.

There is no particular limitation to the method for preparing the cured film forming composition according to the present embodiment. The preparation method, for example, includes mixing predetermined amounts of components (A) and (C) and further component (D) into a solution of component (B) dissolved in a solvent, to obtain a uniform solution. If necessary, another additive may be further added and mixed at an appropriate stage of this preparation method.

In the preparation of the cured film forming composition according to the present embodiment, the solution of the specific copolymer obtained by a polymerization reaction in a solvent may be used as such. In this case, for example, components (A), (C), and (D) and other optional components may be added to the solution of the prepared acrylic polymer component (B), to obtain a uniform solution. In this instance, for the purpose of controlling the concentration of the composition, a solvent may be further added. In this case, the solvent used in the preparation of component (B) and the solvent used for controlling the concentration of the cured film forming composition may be the same or different.

Further, it is preferred that the prepared solution of the cured film forming composition is subjected to filtration using, e.g., a filter having a pore diameter of about 0.2 μm before use.

8. Method for Producing Coating Film and Cured Film

The resin composition for forming a cured film of the present invention is applied onto a general-purpose plastic substrate of, for example, polypropylene, polyethylene, polycarbonate, polyethylene terephthalate, polyether sulfone, polyethylene naphthalate, or polyimide, or a glass substrate by, for example, a dipping method, a spin coating method, a transfer printing method, a roll coating method, an ink-jet method, a spraying method, or brush coating; and then the resultant coating film is dried and subjected to heat treatment using, for example, a hotplate or an oven, to form a cured film for patterning, which can be used as an underlayer film for forming an image or an insulating film.

There is no particular limitation to the method for the heat treatment. It includes heat treatment performed using a hotplate or an oven in an appropriate atmosphere, specifically, for example, in the air, in an inert gas, such as nitrogen gas, or in vacuum.

The baking temperature is preferably 200° C. or lower for suppressing the decomposition of the photo-acid generator as component (C) and of the structure of formula (1) of component (A).

The baking may be conducted while altering the temperature in two stages or more. Such a stepwise baking would further enhance the uniformity of the obtained film.

In the case the cured film of the present invention produced as mentioned above is used as an underlayer film for forming an image, the patterning properties of the film after irradiated with an ultraviolet light would sometimes become poor if the film is too thin, and the uniformity of the surface of the film would sometimes be deteriorated if the film is too thick. Therefore, the thickness of the cured film ranges preferably 5 to 1,000 nm, more preferably 10 to 800 nm, and most preferably 20 to 500 nm.

Further, the cured film of the present invention can function as an insulating film when it has satisfactorily high insulating properties. In such a case, for example, in an organic FET element, the cured film is disposed directly on a gate electrode to be used as a gate insulating film. In this instance, for the purpose of ensuring the insulating properties, it is desired that the cured film is thicker than the film used as the above-mentioned underlayer film for forming an image. The thickness of the cured film ranges preferably 20 to 1,000 nm, more preferably 50 to 800 nm, and most preferably 100 to 500 nm.

As mentioned above, the cured film of the present invention is formed as follows. The resin composition of the present invention is applied onto a substrate so that the fluorine-rich polymer (component (A)) and the fluorine-poor polymer (component (B)) form two layers or a concentration gradient, and the resultant undried coating film is dried by heating, to form a cured film for patterning. In this instance, crosslinking occurs between the fluorine-rich polymers, between the fluorine-poor polymers, or between the fluorine-rich polymer and the fluorine-poor polymer. The crosslinking turns the cured film for patterning to be insoluble in an image forming liquid, and fixes gradient distribution of the fluorine-poor and fluorine-rich polymers along the thickness of the film. In fact, it is impossible or impractical to directly specify the above-mentioned film by the structure or properties of the film.

9. Use as Underlayer Film for Forming Image: Method for Producing Electrode for Forming Image The underlayer film for forming an image in the present invention is irradiated with an ultraviolet light in a pattern form, and subsequently the below-mentioned image forming liquid is applied to the resultant lower layer, to produce an electrode for forming an image.

In the present invention, there is no particular limitation to the method for irradiating the underlayer film for forming an image with an ultraviolet light in a pattern form. Such a method includes irradiating the underlayer film with an ultraviolet light through a mask having an electrode pattern drawn, or drawing an electrode pattern using a laser.

There is no particular limitation to the material for and the form of the mask as long as the region which requires an electrode transmits an ultraviolet light and the other region does not transmit an ultraviolet light.

In this case, generally, an ultraviolet light having a wavelength within the range of from 200 to 500 nm may be used in the irradiation. It is desirable to appropriately select a wavelength through a filter or the like. Specific examples of wavelengths include 248 nm, 254 nm, 303 nm, 313 nm, and 365 nm. An especially preferred wavelength is 365 nm.

When the underlayer film for forming an image in the present invention is irradiated with an ultraviolet light, the surface energy of the film is gradually increased, and then saturated after the film has been irradiated at a satisfactory dose. The increase of the surface energy reduces the contact angle of the film to an image forming liquid. As the result, the film acquires an improved wettability with the image forming liquid in the ultraviolet light irradiated area.

Therefore, application of the image forming liquid to the underlayer film for forming an image in the present invention after being irradiated with an ultraviolet light allows the image forming liquid to self-systematically form a pattern along the pattern form drawn in the underlayer film for forming an image as a difference of the surface energy, thereby production of an electrode with an intended pattern form would be achieved.

For this reason, it is necessary to irradiate the film with an ultraviolet light at an irradiation dose sufficiently change the contact angle of the underlayer film for forming an image to the image forming liquid. From the viewpoint of the energy efficiency and the reduction of the time for the production process, the irradiation dose is preferably 40 $J/cm^2$ or less, more preferably 20 $J/cm^2$ or less, and most preferably 10 $J/cm^2$ or less.

Further, with respect to the contact angle of the underlayer film for forming an image to the image forming liquid, larger the difference in the contact angle between the ultraviolet light irradiated area and the unirradiated area, easier the patterning. That would make it possible to process an electrode into a complicated pattern or a very fine pattern form. When a solution having a low surface tension is used, the difference in the contact angle of the film to the solution between the exposed portion and the unexposed portion is preferably 5° or more, more preferably 10° or more, and most preferably 20° or more. However, it is preferred to appropriately optimize the difference, taking into consideration the method for applying the image forming liquid, the surface tension of the image forming liquid, the degree of definition of the image, and the flatness of the film.

For the same reason, it is preferred that the contact angle to the image forming liquid in the ultraviolet light unirradiated area is 30° or more and that in the ultraviolet light irradiated area is 20° or less.

The image forming liquid in the present invention refers to such a coating liquid that the liquid is applied to a substrate, then the solvent contained therein is evaporated, and the resultant film can be used as a functional thin film. For example, it includes an image forming liquid having a charge transporting substance dissolved or uniformly dispersed in at least one solvent. The term "charge transporting property" has the same meaning as that of electrical conductivity, and means any of hole transporting property, electron transporting property, and charge transporting property for both holes and electrons.

There is no particular limitation to the above-mentioned charge transporting substance as long as the substance has electrical conductivity such that holes or electrons can be transported. Examples of the charge transporting substances include fine particles of a metal, such as gold, silver, copper, or aluminum; inorganic materials, such as carbon black, fullerenes, and carbon nanotubes; and organic it conjugated polymers, such as polythiophene, polyaniline, polypyrrole, polyfluorene, and derivatives thereof.

Further, for the purpose of improving the charge transporting ability of the charge transporting substance, a charge accepting substance, such as a halogen, a Lewis acid, a protonic acid, or a transition metal compound (specific examples include $Br_2$, $I_2$, $Cl_2$, $FeCl_3$, $MoCl_5$, $BF_4$, $AsF_6$, $SO_4$, $HNO_4$, $H_2SO_4$, and polystyrenesulfonic acid), or a charge donating substance, such as an alkali metal or alkylammonium ions (specific examples include Li, Na, K, Cs, tetraethyleneammonium, and tetrabutylammonium), may be further added as a dopant to the image forming liquid.

There is no particular limitation to the solvent for the image forming liquid as long as it can dissolve or uniformly disperse therein the charge transporting substance or dopant. From the viewpoint of obtaining an accurate electrode image (pattern), the surface tension of the image forming liquid ranges preferably 25 to 50 mN/m. A surface tension of the image forming liquid far lower than the above-mentioned range would not result in a sufficiently large contact angle of the ultraviolet light unirradiated area to the image forming liquid. A surface tension of the image forming liquid far higher than the above-mentioned range would result in a higher contact angle of the ultraviolet light irradiated area to the image forming liquid, so that the irradiation dose of an ultraviolet light is disadvantageously inevitably increased.

There is no particular limitation to the solvent for the image forming liquid. Various organic solvents, such as alcohols, ketones, ethers, esters, aromatic hydrocarbons, and glycols, may be used. Examples of alcohols include methanol, isopropanol, normal-butanol, isobutanol, secondary-butanol, isoamyl alcohol, and octanol. Examples of ketones include acetone, methyl ethyl ketone, methyl isobutyl ketone, cyclohexanone, and diacetone alcohol. Examples of ethers include ether-isopropyl ether, dioxane, methyl cellosolve, ethyl cellosolve, and butyl cellosolve. Examples of esters include ethyl acetate, butyl acetate, isobutyl acetate, amyl acetate, cellosolve acetate, and fatty acid methyl ester. Examples of aromatic hydrocarbons include benzene, toluene, xylene, and mesitylene. Examples of aliphatic hydrocarbons include normal-hexane, isohexane, cyclohexane, mineral turpentine, and normal-pentane. Examples of glycols include ethylene glycol, diethylene glycol, propylene glycol, dipropylene glycol, and propylene glycol monomethyl ether.

Further, polar solvents, such as N,N-dimethylformamide, N,N-dimethylacetamide, 2-pyrrolidone, N-methyl-2-pyrrolidone, N-ethyl-2-pyrrolidone, N-vinyl-2-pyrrolidone, N-methylcaprolactam, dimethyl sulfoxide, and tetramethylurea, are preferred from the viewpoint of their good solubility for the organic charge transporting substance. It is preferred to use the above solvents so as to give little damage the underlayer film for forming an image in the present invention.

Further, a solvent having especially high surface tension, such as water, may also be used, but it is preferred to add, for example, a surfactant to such a solvent so as to adjust the surface tension.

The concentration of the charge transporting substance in the image forming liquid ranges preferably 0.01 to 30% by mass, more preferably 0.1 to 10% by mass, and most preferably 1 to 5% by mass.

Specific examples of the image forming liquids in the present invention include conductive polymer solutions, such as Baytron (registered trademark) P (polyethylenedioxythiophene, manufactured by Bayer AG), and silver fine particles dispersions, such as DOTITE XA-9069 (manufactured by Fujikura Kasei Co., Ltd.), W4A (manufactured by Sumitomo Electric Industries, Ltd.), and NPS-J (manufactured by Harima Chemicals, Inc.).

The electrode in the present invention is produced by applying the image forming liquid onto the underlayer film for forming an image in the present invention to form an image, and then evaporating the solvent. There is no particular limitation to the method for evaporating the solvent. A uniform surface of the film can be obtained by performing evaporation using a hotplate or an oven in an appropriate atmosphere, specifically, for example, in the air, in an inert gas, such as nitrogen gas, or in vacuum.

There is no particular limitation to the temperature for evaporation of the solvent. The evaporation is preferably conducted at 40 to 250° C. From the viewpoint of, for example, maintaining the form of the underlayer film for forming an image and achieving uniformity of the thickness of the film, the temperature may be changed in two stages or more.

In the underlayer film for forming an image in the present invention, the non-image formed portion still carries the remainder of the unreacted photo-acid generator and the liquid repellent group that has not been eliminated. For increasing the reliability of the underlayer film for forming an image, after applying the image forming liquid, the reaction in the non-image formed portion of the underlayer film for forming an image may be encouraged by ultraviolet light irradiation, heating, or ultraviolet light irradiation and then heating.

The electrode produced from the image forming liquid is used not only as a wiring for connecting together electronic devices, but also as an electrode for electronic devices, such as a filed effect transistor, a bipolar transistor, various diodes, and various sensors.

The electronic device in the present invention has an electrode produced from an image forming liquid, which is provided on the above-described underlayer film for forming an image in the present invention.

An example in which the underlayer film for forming an image in the present invention is used in an organic FET element is shown below, but the present invention is not limited to this example.

A glass substrate having an ITO electrode formed on one of the major surface is first provided. It is preferred that the substrate is preliminarily cleaned by washing with a liquid, such as a detergent, an alcohol, or pure water, and, immediately before application, subjected to surface treatment, such as an ozone treatment or an oxygen-plasma treatment. The resin composition for forming a cured film of the present invention is applied onto the surface of the substrate having an ITO electrode in accordance with the procedure mentioned above in "Method for Producing Coating Film and Cured Film", to form a film. The thickness of the layer is most preferably 100 to 1,000 nm in view of the drive voltage and electrical insulating properties. Then, the resultant film is irradiated with an ultraviolet light in a pattern form using, for example, a mask.

Subsequently, an image forming liquid using a low surface tension solvent, such as PGME, is applied to the surface of the underlayer film for forming an image. The applied image forming liquid quickly spreads over the lyophilic portion (ultraviolet light irradiated area) so as to repel the liquid repellent portion (ultraviolet light unirradiated area) and is stabilized. The film of the liquid is dried to form patterned source and drain electrodes. There is no particular limitation to the method for applying the image forming liquid. The method includes a spin coating method and a casting method. Preferred are an ink-jet printing method and a spray coating method, which are advantageous in their capability of easily controlling the amount of the liquid applied.

Finally, as an active layer for an organic FET, a film is formed from an organic semiconductor material, such as pentacene or polythiophene, completing the production of an organic FET. There is no particular limitation to the method for forming a film from the organic semiconductor material. The method includes vacuum evaporation, a solution spin coating method, a casting method, an ink-jet printing method, and a spray coating method.

The thus produced organic FET is advantageous in marked reduction of the steps of the production process therefor. It is also advantageous in permitting production of organic FET having a shorter channel than that obtained by a mask evaporation method, to make it possible to take out a large amount of electric current even in the case using an organic semiconductor material having low mobility as an active layer.

EXAMPLES

Hereinbelow, the present embodiment will be described in more detail with reference to the following Examples, which should not be construed as limiting the scope of the present invention.

[Components of Compositions Used in Examples and Others and Abbreviations Thereof]

The components of compositions used in the following Examples and Comparative Examples are as shown below. The synthesis methods for FMAA and CL1 are described later.

<Raw Materials for Specific Polymer>

HPMA: 4-Hydroxyphenyl methacrylate

HEMA: 2-Hydroxyethyl methacrylate

PEGMA: Poly(ethylene glycol) methacrylate; average $M_n$: 360 (manufactured by

SIGMA-ALDRICH Japan Co., LLC.)

GLM: Glycerol monomethacrylate

BMAA: N-Butoxymethylacrylamide

MOI-BP: 2-[(3,5-Dimethylpyrazolyl)carbonylamino]ethyl methacrylate

AIBN: α,α'-Azobisisobutyronitrile

<Other Polymers>

HPC-SSL: Hydroxypropyl cellulose (manufactured by Nippon Soda Co., Ltd.)

F9MAA: Compound represented by the following formula (A1):

[Formula 22]

(A1)

F7MAA: Compound represented by the following formula (A2):

[Formula 23]

(A2)

F13MAA: Compound represented by the following formula (A3):

[Formula 24]

(A3)

<Crosslinking Agent Raw Material>

Karenz MOI-DEM (manufactured by Showa Denko K.K.): Compound represented by the following formula (D1):

[Formula 25]

(D1)

<Crosslinking Agent>

CL1: Compound represented by the following formula (D2):

[Formula 26]

(D2)

<Photo-Acid Generator>

As a photo-acid generator, Irgacure PAG103 represented by formula (C1) (manufactured by BASF AG) and Irgacure PAG121 represented by formula (C2) (manufactured by BASF AG) were used.

[Formula 27]

(C1)

[Formula 28]

(C2)

<Solvent>

Each of the cured film forming compositions in Examples and Comparative Examples contained a solvent. As the solvent, propylene glycol monomethyl ether (PM-P) and propylene glycol monomethyl ether acetate (PMA-P) were used.

[Determination of Molecular Weight of Polymer]

The determination of the molecular weight of the polymer was conducted using GPC System, manufactured by JASCO Corporation, as an apparatus and using Shodex (registered trademark) KF-804L and 803L as a column under the conditions shown below.

Column oven: 40° C.
Flow rate: 1 ml/minute
Eluent: Tetrahydrofuran

Synthesis Example 1

Synthesis of Compound F9MAA Represented by Formula (A1)

[Formula 29]

(A1)

[Formula 30]

[3]

In a 200 ml three-neck flask were placed N-hydroxymethylacrylamide [1] (10.0 g, 98.91 mmol), 3,3,4,4,5,5,6,6,6-nonafluorohexan-1-ol [2] (13.1 g, 49.46 mmol), phosphoric acid (0.24 g, 2.47 mmol), 2,6-di-tertiary-butyl-4-methylphenol (0.11 g, 0.49 mmol), and tetrahydrofuran (54.6 g). The resultant mixture was stirred at 50° C. for 20 hours. The progress of the reaction was confirmed by HPLC, and then hexane (300 g) was added to the obtained solution. The resultant mixture was washed with ion-exchanged water (100 g) three times using a separatory funnel. Then, the mixture was washed with a saturated aqueous solution of sodium hydrogencarbonate (100 g), and concentrated by means of an evaporator to obtain 8.38 g of compound [3].

Synthesis Example 2

Synthesis of Compound F7MAA Represented by Formula (A2)

[Formula 31]

(A2)

[Formula 32]

[3]

In a 200 ml three-neck flask were placed N-hydroxymethylacrylamide [1] (10.0 g, 98.91 mmol), 2,2,3,3,4,4,4-heptafluoro-1-butanol [2] (9.89 g, 49.46 mmol), phosphoric acid (0.24 g, 2.47 mmol), 2,6-di-tertiary-butyl-4-methylphenol (0.11 g, 0.49 mmol), and tetrahydrofuran (54.6 g). The resultant mixture was stirred at 50° C. for 20 hours. The progress of the reaction was confirmed by HPLC, and then hexane (300 g) was added to the obtained solution. The resultant mixture was washed with ion-exchanged water (100 g) three times using a separatory funnel. Then, the mixture was washed with a saturated aqueous solution of sodium hydrogencarbonate (100 g), and concentrated by means of an evaporator to obtain 6.83 g of compound [3].

Synthesis Example 3

Synthesis of Compound F13MAA Represented by Formula (A3)

[Formula 33]

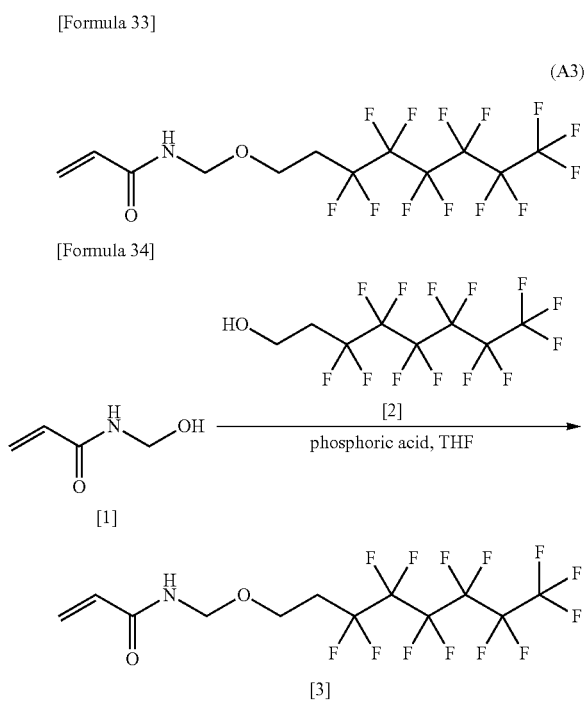

[Formula 34]

In a 200 ml three-neck flask were placed N-hydroxymethylacrylamide [1] (10.0 g, 98.91 mmol), 2-(perfluorohexyl)ethanol [2] (18.0 g, 49.46 mmol), phosphoric acid (0.24 g, 2.47 mmol), 2,6-di-tertiary-butyl-4-methylphenol (0.11 g, 0.49 mmol), and tetrahydrofuran (54.6 g). The resultant mixture was stirred at 50° C. for 20 hours. The progress of the reaction was confirmed by HPLC, and then hexane (300 g) was added to the obtained solution. The resultant mixture was washed with ion-exchanged water (100 g) three times using a separatory funnel. Then, the mixture was washed with a saturated aqueous solution of sodium hydrogencarbonate (100 g), and concentrated by means of an evaporator to obtain 10.8 g of compound [3].

Synthesis Example 4

Synthesis of Compound CL1 Represented by Formula (D2)

[Formula 35]

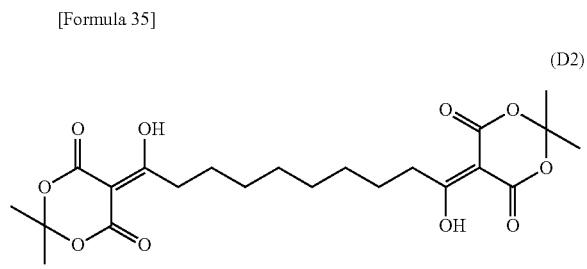

[Formula 36]

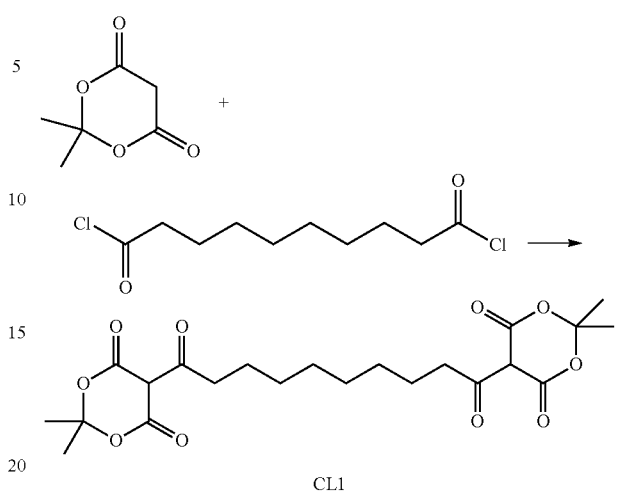

In a nitrogen gas atmosphere, 393 ml of dehydrated methylene chloride, 33.4 g (23.2 mmol) of Meldrum's acid, and 36.7 g (30.0 mol) of N,N-dimethyl-4-aminopyridine were charged at 0° C. To the resultant mixture was dropwise added a solution obtained by dissolving 27.7 g (11.6 mol) of sebacoyl chloride in 60 ml of dehydrated methylene chloride. After completion of the dropwise addition, the temperature of the resultant mixture was gradually increased and the mixture was stirred at room temperature for 20 hours. Then, the mixture was washed once with a mixed solution of 70 ml of 2 N hydrochloric acid and 20 ml of water. The resultant organic layer was washed once with a mixed solution of 25 nil of 2 N hydrochloric acid and 200 ml of water. The organic layer was dried over 10 g of magnesium sulfate. Then, the magnesium sulfate was removed by filtration. The resultant filtrate was concentrated, and the obtained crude product was dissolved in 112 g of acetone while heating, and then cooled and the deposited crystals were dried to obtain a pale yellow solid CL1 (21.9 g (4.81 mol); yield: 41.5%). The structure of this compound was confirmed by the below-shown spectral data obtained by a $^1$H-NMR analysis.

$^1$H-NMR (CDCl$_3$): δ3.06 (t, 4H), 1.74-1.66 (m, 16H), 1.43-1.34 (m, 8H).

Polymerization Example 1

P1: F9MAA/HEMA 56/44

2.56 g of F9MAA, 2.0 g of HEMA, and 0.3 g of AIBN as a polymerization catalyst were dissolved in 41.2 g of PMA-P and reacted at 80° C. for 20 hours to obtain an acrylic copolymer solution (solids concentration: 10% by mass) (P1). The obtained acrylic copolymer had an Mn of 5,872 and an Mw of 8,555.

Polymerization Example 2

P2: BMAA/HEMA 80/20

8.0 g of BMAA, 2.0 g of HEMA, and 0.3 g of AIBN as a polymerization catalyst were dissolved in 41.2 g of PM-P and reacted at 80° C. for 20 hours to obtain an acrylic copolymer solution (solids concentration: 20% by mass) (P2). The obtained acrylic copolymer had an Mn of 3,789 and an Mw of 7,514.

Polymerization Example 3

P3: F9MAA/HPMA/HEMA 18/55/27

1.28 g of F9MAA, 4.0 g of HPMA, 2.0 g of HEMA, and 0.3 g of AIBN as a polymerization catalyst were dissolved in 41.2 g of PMA-P and reacted at 80° C. for 20 hours to obtain an acrylic copolymer solution (solids concentration: 15% by mass) (P3). The obtained acrylic copolymer had an Mn of 7,020 and an Mw of 7,971.

Polymerization Example 4

P4: BMAA/HPMA/HEMA 40/40/20

4.0 g of BMAA, 4.0 g of HPMA, 2.0 g of HEMA, and 0.3 g of AIBN as a polymerization catalyst were dissolved in 41.2 g of PM and reacted at 80° C. for 20 hours to obtain an acrylic copolymer solution (solids concentration: 20% by mass) (P4). The obtained acrylic copolymer had an Mn of 10,103 and an Mw of 25,498.

Polymerization Example 5

P5: MOI-DEM 100

10.0 g of Karenz MOI-DEM (manufactured by Showa Denko K.K.) and 0.3 g of AIBN as a polymerization catalyst were dissolved in 41.2 g of PM and reacted at 80° C. for 20 hours to obtain an acrylic copolymer solution (solids concentration: 20% by mass) (P5). The obtained acrylic copolymer had an Mn of 17,279 and an Mw of 54,273.

Polymerization Example 6

P6: F9MAA/PEGMA 56/44

2.56 g of F9MAA, 2.0 g of PEGMA, and 0.3 g of AIBN as a polymerization catalyst were dissolved in 12.2 g of PM-P and 12.2 g of PMA-P and reacted at 80° C. for 20 hours to obtain an acrylic copolymer solution (solids concentration: 20% by mass) (P6). The obtained acrylic copolymer had an Mn of 22,262 and an Mw of 50,083.

Polymerization Example 7

P7: F9MAA/GLM 56/44

2.56 g of F9MAA, 2.0 g of GLM, and 0.3 g of AIBN as a polymerization catalyst were dissolved in 12.2 g of PM-P and 12.2 g of PMA-P and reacted at 80° C. for 20 hours to obtain an acrylic copolymer solution (solids concentration: 20% by mass) (P7). The obtained acrylic copolymer had an Mn of 23,029 and an Mw of 51,421.

Polymerization Example 8

P8: F7MAA/HEMA 56/44

2.56 g of F7MAA, 2.0 g of HEMA, and 0.3 g of AIBN as a polymerization catalyst were dissolved in 12.2 g of PM-P and 12.2 g of PMA-P and reacted at 80° C. for 20 hours to obtain an acrylic copolymer solution (solids concentration: 20% by mass) (P8). The obtained acrylic copolymer had an Mn of 14,352 and an Mw of 28,460.

Polymerization Example 9

P9: F13MAA/HEMA 56/44

2.56 g of F13MAA, 2.0 g of HEMA, and 0.3 g of AIBN as a polymerization catalyst were dissolved in 12.2 g of PM-P and 12.2 g of PMA-P and reacted at 80° C. for 20 hours to obtain an acrylic copolymer solution (solids concentration: 20% by mass) (P9). The obtained acrylic copolymer had an Mn of 12,074 and an Mw of 19,702.

Polymerization Example 10

P10: F9MAA/MOI-BP/HEMA 40/40/20

4.0 g of F9MAA, 4.0 g of MOI-BP, 2.0 g of HEMA, and 0.5 g of AIBN as a polymerization catalyst were dissolved in 20.6 g of PM-P and 20.6 g of PMA-P and reacted at 80° C. for 20 hours to obtain an acrylic copolymer solution (solids concentration: 20% by mass) (P10). The obtained acrylic copolymer had an Mn of 14,475 and an Mw of 43,907.

Polymerization Example 11

P11: BMAA/MOI-BP/HEMA 40/40/20

4.0 g of BMAA, 4.0 g of MOI-BP, 4.0 g of HEMA, and 0.7 g of AIBN as a polymerization catalyst were dissolved in 41.2 g of PM-P and reacted at 80° C. for 20 hours to obtain an acrylic copolymer solution (solids concentration: 20% by mass) (P11). The obtained acrylic copolymer had an Mn of 20,277 and an Mw of 133,030.

[Preparation of Cured Film Forming Composition]

Each of the cured film forming compositions in Examples and Comparative Examples having the formulations shown in Table 1 was prepared. The solids concentration of each composition was 5% by weight. Then, using each of the cured film forming compositions prepared, cured films were formed, and, with respect to each of the obtained cured films, the measurement of a contact angle and the evaluation of solvent resistance to n-nonane and PMA-P were conducted. The formulation shown in Table 1 indicates the ratio of the components in terms of solids content.

TABLE 1

| | Component (A) | | Component (B) | | Component (D) | | Component (C) | | Solvent | | |
|---|---|---|---|---|---|---|---|---|---|---|---|
| | | Amount | | Amount | | Amount | | Amount | | | |
| No | Type | (Parts by mass) | Type | (Parts by mass) | Type | (Parts by mass) | Type | (Parts by mass) | Solvent 1 | Solvent 2 | Solvent 1:2 ratio |
| Example 1 | P1 | 10 | P2 | 90 | CL1 | 20 | PAG121 | 5 | PM-P | PMA-P | 50:50 |
| Example 2 | P1 | 10 | P2 | 90 | CL1 | 20 | PAG103 | 5 | PM-P | PMA-P | 50:50 |
| Example 3 | P1 | 10 | P2 | 90 | CL1 | 20 | PAG121 | 15 | PM-P | PMA-P | 50:50 |
| Example 4 | P1 | 10 | P2 | 90 | CL1 | 50 | PAG121 | 5 | PM-P | PMA-P | 50:50 |
| Example 5 | P1 | 10 | P2 | 90 | CL1 | 5 | PAG121 | 5 | PM-P | PMA-P | 50:50 |
| Example 6 | P1 | 10 | P2 | 90 | P5 | 20 | PAG121 | 5 | PM-P | PMA-P | 50:50 |
| Example 7 | P1 | 10 | P2 | 90 | | | PAG121 | 5 | PM-P | PMA-P | 50:50 |
| Example 8 | P1 | 10 | P4 | 90 | P5 | 20 | PAG121 | 5 | PM-P | PMA-P | 50:50 |
| Example 9 | P3 | 10 | P4 | 90 | CL1 | 20 | PAG121 | 5 | PM-P | PMA-P | 50:50 |
| Example 10 | P6 | 10 | P4 | 90 | P5 | 20 | PAG121 | 5 | PM-P | PMA-P | 50:50 |

TABLE 1-continued

|  |  | Component (A) |  | Component (B) |  | Component (D) |  | Component (C) | Solvent | | |
|---|---|---|---|---|---|---|---|---|---|---|---|
|  |  | Amount |  | Amount |  | Amount |  | Amount | | | |
| No | Type | (Parts by mass) | Type | (Parts by mass) | Type | (Parts by mass) | Type | (Parts by mass) | Solvent 1 | Solvent 2 | Solvent 1:2 ratio |
| Example 11 | P7 | 10 | P4 | 90 | P5 | 20 | PAG121 | 5 | PM-P | PMA-P | 50:50 |
| Example 12 | P8 | 10 | P4 | 90 | P5 | 20 | PAG121 | 5 | PM-P | PMA-P | 50:50 |
| Example 13 | P9 | 10 | P4 | 90 | P5 | 20 | PAG121 | 5 | PM-P | PMA-P | 50:50 |
| Example 14 | P1 | 10 | HPC-SSL | 90 | P5 | 20 | PAG121 | 5 | PM-P | PMA-P | 50:50 |
| Example 15 | P10 | 10 | P11 | 90 |  |  | PAG121 | 5 | PM-P | PMA-P | 50:50 |
| Comparative Example 1 |  |  | P2 | 100 | CL1 | 20 | PAG121 | 5 | PM-P | PMA-P | 50:50 |
| Comparative Example 1 | P1 | 10 | P2 | 90 | CL1 | 20 |  |  | PM-P | PMA-P | 50:50 |

[Evaluation of Solvent Resistance]

Each of the cured film forming compositions in Examples and Comparative Examples was spin-coated onto a silicon wafer using a spin coater at 850 rpm for 30 seconds. The spin-coated film was then dried by heating on a hotplate at a temperature of 140° C. for 120 seconds to form a coating film having a thickness of 200 nm. The thickness of the film was measured using F20, manufactured by FILMETRICS Japan, Inc. Two regions were defined in this coating film, and one region was irradiated with an ultraviolet light having a light intensity of 100 mJ/cm$^2$ at 365 nm for a predetermined time by means of ultraviolet light radiation apparatus PLA-600FA, manufactured by Canon Inc., wherein the direction of the ultraviolet light was perpendicular to the surface of the coating film (hereinafter, this region is referred to as "exposed portion", and the other region is referred to as "unexposed portion"). Then, the film was post-baked on a hotplate at 120° C. for 120 seconds. The resultant cured film having the unexposed portion and exposed portion was immersed in n-nonane for one minute, and separately immersed in PMA-P for one minute. The thicknesses of the film before and after the immersion were measured to determine a residual film ratio. The solvent resistance was evaluated from the residual film ratio.

[Results of Evaluation]

The results of the above evaluation are, as mentioned above, shown in Table 2.

TABLE 2

|  | Residual film ratio | | | |
|---|---|---|---|---|
|  | n-nonane | | PMA-P | |
| No | Unexposed portion | Expoed portion | Unexposed portion | Exposed portion |
| Example 1 | 100% | 100% | 89% | 100% |
| Example 2 | 99% | 100% | 89% | 100% |
| Example 3 | 95% | 100% | 83% | 100% |
| Example 4 | 96% | 100% | 91% | 100% |
| Example 5 | 99% | 100% | 40% | 100% |
| Example 6 | 100% | 100% | 67% | 100% |
| Example 7 | 98% | 100% | 1% | 100% |
| Example 8 | 100% | 100% | 100% | 100% |
| Example 9 | 100% | 100% | 100% | 100% |
| Example 10 | 100% | 100% | 100% | 100% |
| Example 11 | 100% | 100% | 100% | 100% |
| Example 12 | 100% | 100% | 100% | 100% |
| Example 13 | 100% | 100% | 100% | 100% |
| Example 14 | 100% | 100% | 82% | 100% |
| Example 15 | 100% | 100% | 100% | 100% |
| Comparative Example 1 | 99% | 100% | 90% | 100% |
| Comparative Example 2 | 99% | 100% | 91% | 91% |

In all Examples 1 to 15 and Comparative Examples 1 and 2, high solvent resistance was exhibited with respect to n-nonane. In Examples 1 to 6 and 8 to 14 and Comparative Examples 1 and 2 in which a crosslinking agent as component (D) was added, and in Example 15 in which a crosslinkable monomer was used in component (A), high solvent resistance was exhibited also with respect to PMA-P.

Further, in Examples 1 to 15, due to the crosslinking effect of the liquid repellent group, especially high solvent resistance was exhibited at the exposed portion. In contrast, in Comparative Example 2, no difference in the solvent resistance was observed between the exposed portion and the unexposed portion. The solvent resistance to PMA-P at the exposed portion in Comparative Example 2 was poorer than that in Examples 1 to 15.

[Determination of Contact Angle]

Each of the cured film forming compositions in Examples and Comparative Examples was applied onto a silicon wafer using a spin coater. The spin-coated film was then dried by heating on a hotplate at a temperature of 140° C. for 120 seconds to form a coating film having a thickness of 200 nm. The thickness of the film was measured using F20, manufactured by FILMETRICS Japan, Inc. Two regions were defined in this coating film, and one region was irradiated with an ultraviolet light having a light intensity of 100 mJ/cm$^2$ at 365 nm for a predetermined time by means of ultraviolet light radiation apparatus PLA-600FA, manufactured by Canon Inc., wherein the direction of the ultraviolet light was perpendicular to the surface of the coating film (hereinafter, this region is referred to as "exposed portion", and the other region is referred to as "unexposed portion"). Then, the film was post-baked on a hotplate at 120° C. for 120 seconds. Then, the contact angle of the unexposed portion and exposed portion of the resultant coating film was measured. The measurement of a contact angle was conducted in an environment at a constant temperature and at a constant humidity (25±2° C., 50% RH±5%) using Automatic Contact Angle Meter CA-W (manufactured by Kyowa Interface Science Co., Ltd.). The contact angle to PMA-P or n-nonane was determined after the applied PMA-P or n-nonane was left to stand for 5 seconds.

[Results of Evaluation]

The results of the above evaluation are, as mentioned above, shown in Table 3.

TABLE 3

| No | Contact angle | | | |
|---|---|---|---|---|
| | n-nonane | | PGMEA | |
| | Unexposed portion | Exposed portion | Unexposed portion | Exposed portion |
| Example 1 | 47° | <5° | 28° | 9° |
| Example 2 | 46° | <5° | 29° | <5° |
| Example 3 | 46° | <5° | 29° | <5° |
| Example 4 | 36° | <5° | 23° | <5° |
| Example 5 | 50° | <5° | 38° | 12° |
| Example 6 | 45° | 10° | 32° | 21° |
| Example 7 | 51° | <5° | 16° | 19° |
| Example 8 | 57° | <5° | 46° | <5° |
| Example 9 | 26° | <5° | 18° | <5° |
| Example 10 | 53° | <5° | 47° | <5° |
| Example 11 | 55° | <5° | 56° | <5° |
| Example 12 | 47° | <5° | 30° | <5° |
| Example 13 | 61° | <5° | 66° | <5° |
| Example 14 | 54° | <5° | 49° | <5° |
| Example 15 | 50° | 16° | 42° | 27° |
| Comparative Example 1 | <5° | <5° | <5° | <5° |
| Comparative Example 2 | 47° | 47° | 30° | 30° |

In all Examples 1 to 15, the difference in contact angle to n-nonane between the unexposed and exposed portions was large. Especially in Examples 1 to 6 and 8 to 15 in which a crosslinking agent was used, the difference in contact angle also to PMA-P between the unexposed and exposed portions was large.

In contrast, in Comparative Examples 1 and 2, no difference in contact angle was observed between the exposed and unexposed portions.

INDUSTRIAL APPLICABILITY

As apparent from the foregoing, the cured film obtained from the cured film forming composition of the present invention had excellent performance in respect of both the solvent resistance and the contrast between lyophilicity and liquid repellency, and it exhibited the effects on various organic solvents including n-nonane and PMA-P.

The invention claimed is:

1. A resin composition for forming a cured film, comprising:

as component (A), a polymer comprising a structural unit derived from a first monomer having a structure of formula (1)

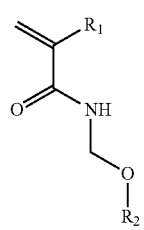

(1)

wherein $R^1$ represents hydrogen or a methyl group, and $R^2$ represents a fluorine-containing group capable of being eliminated together with an oxygen atom to which the fluorine-containing group is bonded;

as component (B), a polymer other than component (A), which has a smaller fluorine content based on the weight of the polymer than that of component (A);

a photo-acid generator as component (C); and a solvent.

2. The resin composition for forming a cured film according to claim 1, wherein $R^2$ represents a fluorine-substituted hydrocarbon group, which is optionally branched and/or cyclized, and which is optionally interrupted by an aromatic ring, —O—, —S—, —CO—, —CS—, —NH—, or a combination thereof.

3. The resin composition for forming a cured film according to claim 1, wherein $R^2$ has two or more carbon atoms.

4. The resin composition for forming a cured film according to claim 1, wherein the polymer component (A) further comprises a structural unit derived from a second monomer having a group (group (x)) capable of forming due to heat a covalent bond between the polymers as component (A) or between the polymer component (A) and the polymer component (B).

5. The resin composition for forming a cured film according to claim 1, wherein the polymer component (B) comprises a structural unit derived from a monomer having a group (group (x)) capable of forming due to heat a covalent bond between the polymers as component (B) or between the polymer component (A) and the polymer component (B).

6. The resin composition for forming a cured film according to claim 4, wherein group (x) is at least one group selected from the group consisting of a hydroxyl group, a carboxyl group, an amide group, an alkoxysilyl group, an isocyanate group, a blocked isocyanate group, and a group represented by formula (2):

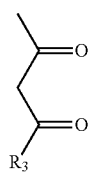

(2)

wherein $R^3$ represents an alkyl group, an alkoxy group, or a phenyl group.

7. The resin composition for forming a cured film according to claim 4, which further comprises, as a component (D), a compound having two or more groups capable of undergoing a thermal reaction with group (x) per molecule.

8. The resin composition for forming a cured film according to claim 1, wherein the polymer component (A) has a fluorine content of 5% by weight or more based on the weight of the polymer.

9. The resin composition for forming a cured film according to claim 1, wherein the polymer component (B) has a fluorine content of less than 5% by weight based on the weight of the polymer.

10. A cured film, which is obtained using the resin composition for forming a cured film according to claim 1, and wherein the cured film has an ultraviolet light exposed portion more lyophilic than an unexposed portion.

11. The cured film according to claim 10, wherein the ultraviolet light exposed portion has a contact angle to propylene glycol monomethyl ether acetate at least 5° greater than that of the unexposed portion.

12. A wiring forming auxiliary layer comprising the cured film of claim 10.

13. A method for the manufacture of a resin composition for forming a cured film comprising use of a copolymer comprising a structural unit derived from a first monomer and a structural unit derived from a second monomer having a group (group (x)) capable of forming due to heat a covalent bond between the polymers as component (A) or between the polymer component (A) and the polymer component (B), wherein the first monomer has a structure of formula (1)

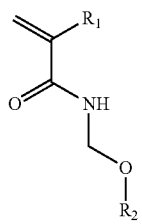

wherein $R^1$ represents hydrogen or a methyl group, and $R^2$ represents a fluorine-containing group capable of being eliminated together with an oxygen atom to which the fluorine-containing group is bonded.

14. A method for the manufacture of a cured film having an ultraviolet light exposed portion more lyophilic than an unexposed portion comprising use of the resin composition for forming a cured film according to claim 1.

15. The method according to claim 14, wherein the ultraviolet light exposed portion has a contact angle to propylene glycol monomethyl ether acetate at least 5° greater than that of the unexposed portion.

16. The resin composition for forming a cured film according to claim 5, wherein group (x) is at least one group selected from the group consisting of a hydroxyl group, a carboxyl group, an amide group, an alkoxysilyl group, an isocyanate group, a blocked isocyanate group, and a group represented by formula (2):

wherein $R^3$ represents an alkyl group, an alkoxy group, or a phenyl group.

17. The resin composition for forming a cured film according to claim 5, which further comprises, as a component (D), a compound having two or more groups capable of undergoing a thermal reaction with group (x) per molecule.

18. A wiring forming auxiliary layer comprising the cured film of claim 11.

* * * * *